(12) United States Patent
Kikuchi et al.

(10) Patent No.: US 12,271,005 B2
(45) Date of Patent: Apr. 8, 2025

(54) SCOPE OPTICAL SYSTEM, IMAGING APPARATUS, AND ENDOSCOPE SYSTEM

(71) Applicant: Sony Group Corporation, Tokyo (JP)

(72) Inventors: Naomichi Kikuchi, Kanagawa (JP); Satoshi Nagae, Tokyo (JP)

(73) Assignee: Sony Group Corporation, Tokyo (JP)

( * ) Notice: Subject to any disclaimer, the term of this patent is extended or adjusted under 35 U.S.C. 154(b) by 80 days.

(21) Appl. No.: 18/311,295

(22) Filed: May 3, 2023

(65) Prior Publication Data

US 2023/0350218 A1    Nov. 2, 2023

Related U.S. Application Data

(63) Continuation of application No. 16/981,698, filed as application No. PCT/JP2019/007059 on Feb. 25, 2019, now Pat. No. 11,675,204.

(30) Foreign Application Priority Data

Mar. 28, 2018 (JP) .................. 2018-061788

(51) Int. Cl.
  *A61B 1/00* (2006.01)
  *A61B 1/04* (2006.01)
  *G02B 27/14* (2006.01)

(52) U.S. Cl.
  CPC ........ *G02B 27/141* (2013.01); *A61B 1/00163* (2013.01); *A61B 1/043* (2013.01); *A61B 1/00009* (2013.01)

(58) Field of Classification Search
  CPC ............ A61B 1/00188; A61B 1/00163; A61B 1/00009; A61B 1/043; G02B 27/141
  (Continued)

(56) References Cited

U.S. PATENT DOCUMENTS 9,835,821 B1 * 12/2017 Yin .................. A61B 1/05
2011/0001061 A1    1/2011 Ishihara
(Continued)

FOREIGN PATENT DOCUMENTS

CN    102414597 A    4/2012
JP    11-337819 A    12/1999
(Continued)

OTHER PUBLICATIONS

International Search Report and Written Opinion mailed on Apr. 9, 2019 for PCT/JP2019/007059 filed on Feb. 25, 2019, 9 pages.

*Primary Examiner* — Timothy J Neal
*Assistant Examiner* — James Edward Boice
(74) *Attorney, Agent, or Firm* — XSENSUS LLP

(57) ABSTRACT

A rigid-scope optical system includes: an image-formation optical system that causes an image in each of wavelength bands to be formed in a predetermined imaging device, the wavelength bands including a fluorescence wavelength band and a visible light wavelength band; and a color-separation-prism optical system having a dichroic film that separates an optical path of light to be imaged into an optical path of the visible light wavelength band and an optical path of the fluorescence wavelength band, in which the image-formation optical system causes the respective images to be formed in a fluorescence imaging device and a visible light imaging device, the fluorescence imaging device and the visible light imaging device being disposed to cause an amount of misalignment to correspond to a difference between an optical path length of fluorescence and an optical path length of visible light.

21 Claims, 20 Drawing Sheets

(58) Field of Classification Search
USPC .......................................................... 600/160
See application file for complete search history.

(56) References Cited

U.S. PATENT DOCUMENTS

| | | |
|---|---|---|
| 2016/0249811 A1 | 9/2016 | Khan et al. |
| 2016/0262602 A1 | 9/2016 | Yu |
| 2018/0000401 A1 | 1/2018 | Kang et al. |
| 2018/0003944 A1 | 1/2018 | Fujii |

FOREIGN PATENT DOCUMENTS

| | | |
|---|---|---|
| JP | 2000-089105 A | 3/2000 |
| JP | 2001166203 A | 6/2001 |
| JP | 2004-240464 A | 8/2004 |
| JP | 2014-138196 A | 7/2014 |
| JP | 6029159 B1 | 11/2016 |
| JP | 2017-053890 A | 3/2017 |
| WO | 2016/114080 A1 | 7/2016 |
| WO | 2017/043000 A1 | 3/2017 |
| WO | 2017/217498 A1 | 12/2017 |

* cited by examiner

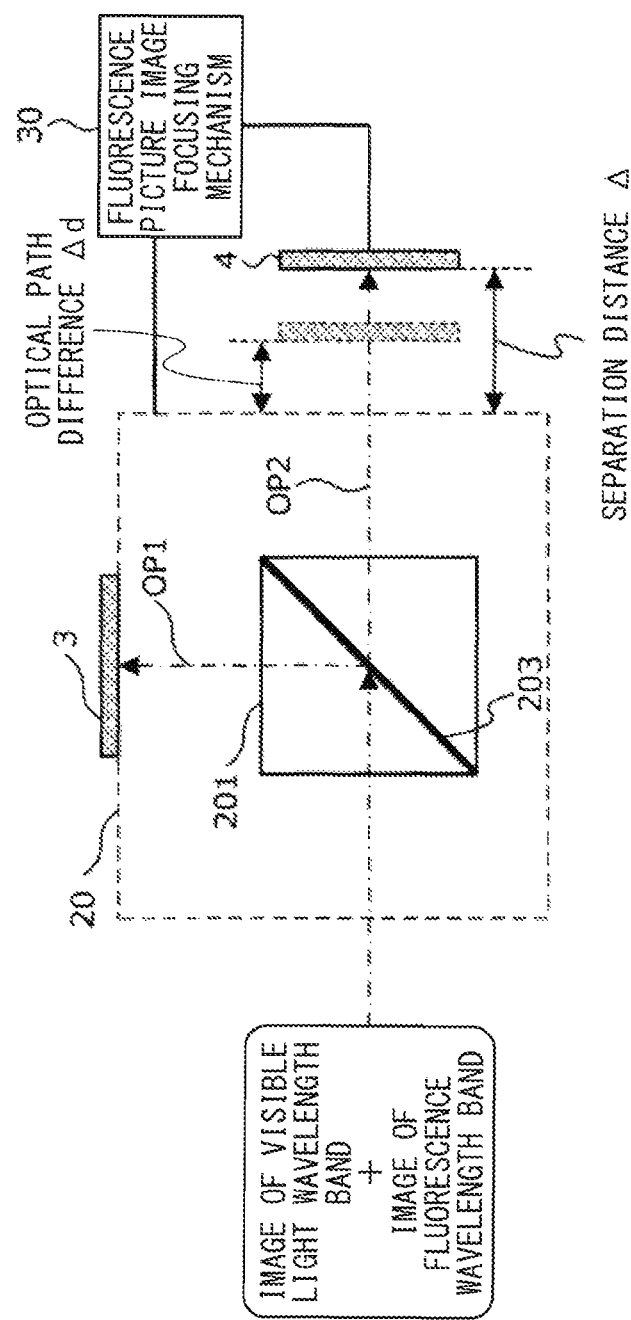

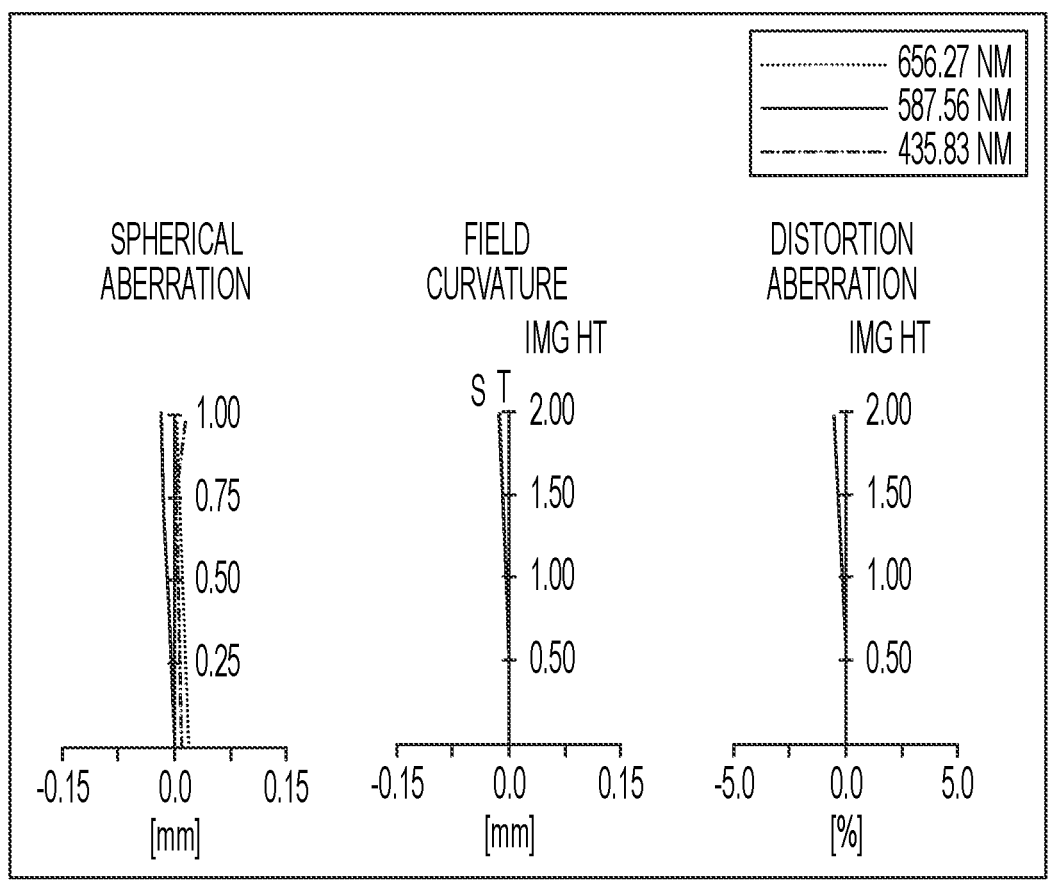

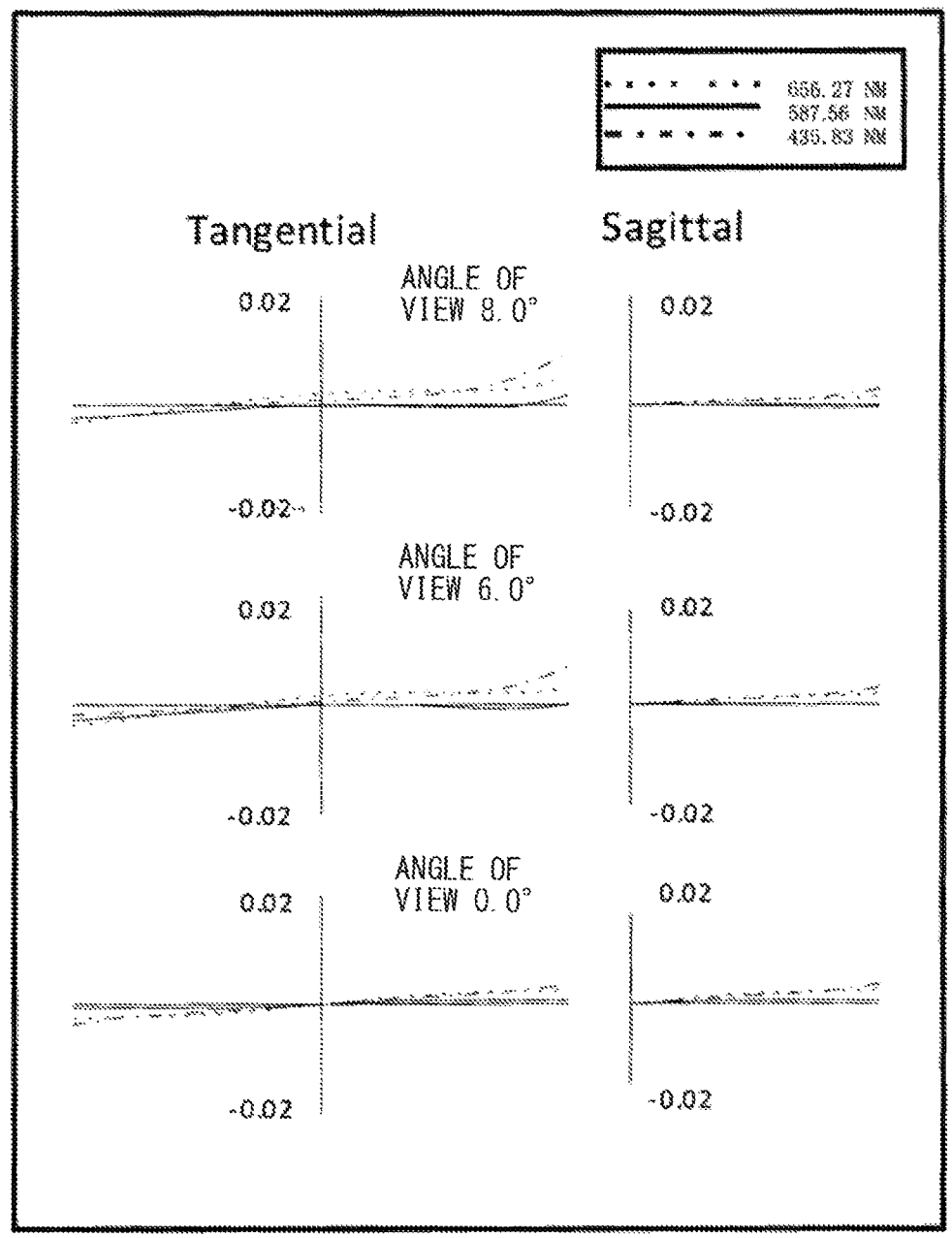

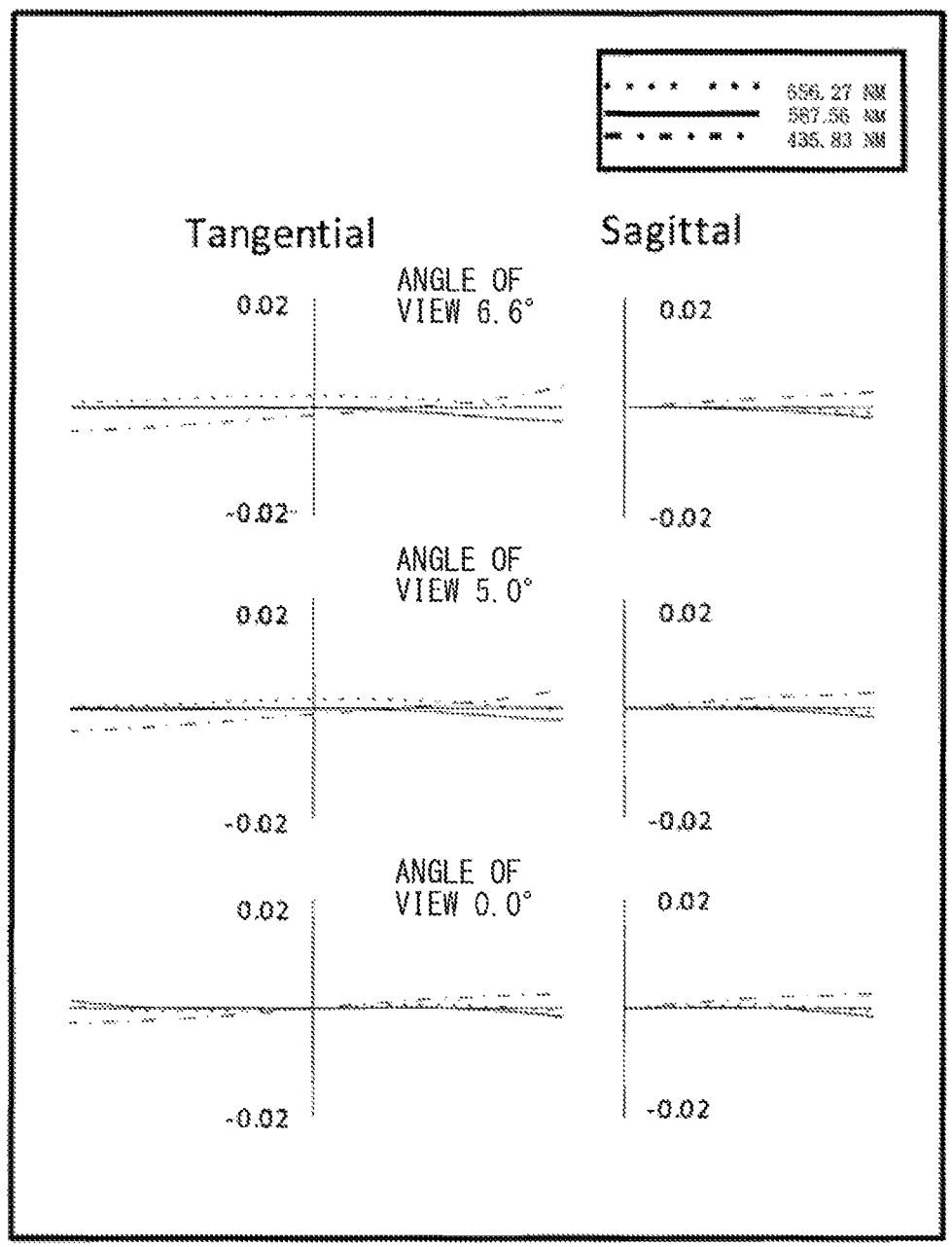

SCOPE OPTICAL SYSTEM, IMAGING APPARATUS, AND ENDOSCOPE SYSTEM

CROSS-REFERENCE TO RELATED APPLICATIONS

The present application is a continuation of U.S. application Ser. No. 16/981,698, filed Sep. 17, 2020, which is based on PCT filing PCT/JP2019/007059, filed Feb. 25, 2019, which claims priority to JP 2018-061788, filed Mar. 28, 2018, the entire contents of each are incorporated herein by reference.

TECHNICAL FIELD

The present disclosure relates to a rigid-scope optical system, an imaging apparatus, and an endoscope system.

BACKGROUND ART

In recent years, in the medical field, there has been an increasing demand for not only observation of an affected area using light belonging to the visible light wavelength band but also observation of an affected area using fluorescence belonging to the near-infrared wavelength band when performing a surgery using an endoscopy. This is because surgery using an ICG (indocyanine green) reagent, which emits fluorescence having a wavelength of 830 to 840 nm by being irradiated with near-infrared excitation light having a wavelength of around 800 nm, as a marker in the body for identifying a site, has begun to become widespread. The above-described ICG reagent is a safe reagent which is not toxic even when injected into the body, and is particularly used for the presence or absence of blood flow in brain surgery, identification of cancer in a sentinel lymph node in breast cancer, etc., and clinical research for endoscopic surgery is proceeding.

However, most of the fluorescent reagents used in the medical field, such as ICG and the like, have very low fluorescence efficiency, so that a highly sensitive camera is used to image a subject of interest (i.e., a site emitting fluorescence). Because ICG-compatible endoscopic camera heads and photographing systems that are available on the market today use, as imaging devices, existing visible light RGB single-plate or three-plate sensors, a sensitivity in the near-infrared wavelength band is not sufficient, and image quality and resolution are not comparable to those of a visible light picture image.

Further, the above-described sensor mainly utilizing R, G, and B is not able to image a visible light ray and a near-infrared ray at a time, and is only able to perform imaging in one of the wavelength bands. Therefore, it is not possible to compare the affected area identified by the near-infrared ray (i.e., fluorescence) with a video of the visible light ray, and there has been a possibility that accuracy of the surgery is decreased due to misalignment of the site caused by the switching.

For ensuring the accuracy of the surgery, there has been proposed an imaging method called a time division method in which a picture image captured under the visible light ray and a picture image captured under the near-infrared ray are simultaneously displayed in a pseudo manner by simultaneously and timely switching modes of a light source and a imaging device every frame. For example, PTL 1 proposes, for achieving imaging in the time division method described above, installing a special band-pass filter in a preceding stage of a visible light RGB sensor, and performing strict switching control between an imaging mode and a light source illumination mode of the sensor.

However, in a case of the technique borrowing an imaging device of the visible light band described in PTL 1, a lens group in which chromatic aberration is corrected specialized for the visible light band is often used, and in such a case, a picture image of the near-infrared wavelength band inevitably becomes blurred due to chromatic aberration. In addition, in the system using the above-described time division format, it is very difficult to focus on each frame by auto-focus every time the switching is performed, and a picture image of one of the wavelength bands is inevitably simultaneously imaged with a poor resolution at all times.

For this reason, as a method of achieving simultaneous acquisition of a picture image of the visible light wavelength band and a picture image of the near-infrared wavelength band in a method other than the time division method, a method has been proposed in which an optical path to which light of an acquired image is guided is branched into an optical path for the visible light wavelength band and an optical path for the near-infrared wavelength band, and then an imaging device for the visible light and an imaging device for the near-infrared light are used (see, for example, PTL 2 and PTL 3).

CITATION LIST

Patent Literature

PTL 1: Japanese Patent No. 6088629
PTL 2: Japanese Unexamined Patent Application Publication No. 2017-53890
PTL 3: Japanese Patent No. 6147455

SUMMARY OF THE INVENTION

Problems to be Solved by the Invention

Here, considering endoscopic observations in the medical field, it is necessary to further increase the resolution of a picture image to be acquired for further improving safety of a procedure performed by a physician or the like. In the case of the technique of the time division method as disclosed in PTL 1: it is demanded to increase the resolution only by design change on the optical system to be used for further increasing the resolution of the picture image, thereby inevitably increasing the number of lenses to be used; and it is necessary to use a glass material having a low anomalous dispersibility for causing the visible light and the near-infrared light to be imaged simultaneously at a high resolution. However, many of the glass materials each having a low abnormal dispersibility are relatively fragile, and there is a concern about reliability in the medical field in which processes such as high temperature disinfection and chemical disinfection are performed at all times. Further, the size of the apparatus itself is increased if the number of lenses used is increased, which reduces the convenience of a user.

In contrast, the methods as disclosed in PTL 2 and PTL 3 are able to maintain reliability of the apparatus and to reduce the size of the apparatus. However, in the method disclosed in PTL 2, for example, no studies have been carried out on an optical system for achieving further higher resolution, such as a 4K resolution. Further, in the optical system disclosed in PTL 3, a size of a prism for branching the optical path is too small, which raises a concern that a flare of an internal reflection of the prism will increase, and it has been difficult to achieve higher resolution.

As described above, there is a current demand for a medical-use imaging apparatus that is able to achieve reduction in size while ensuring reliability as an apparatus, and to obtain a captured picture image having a more excellent resolution, such as a 4K resolution, for example.

Accordingly, in view of the above circumstances, the present disclosure proposes a rigid-scope optical system, an imaging apparatus, and an endoscope system that are able to achieve reduction in size while ensuring reliability as an apparatus, and to achieve further resolution of a captured picture image to be obtained.

Means for Solving the Problems

According to the present disclosure, there is provided a rigid-scope optical system including: an image-formation optical system that causes an image in each of wavelength bands to be formed in a predetermined imaging device, the wavelength bands including a fluorescence wavelength band belonging to a near-infrared light wavelength band and a visible light wavelength band; and a color-separation-prism optical system having a dichroic film that separates an optical path of light to be imaged by the image-formation optical system into an optical path of the visible light wavelength band and an optical path of the fluorescence wavelength band, in which the image-formation optical system causes the respective images to be formed in a fluorescence imaging device and a visible light imaging device, the fluorescence imaging device and the visible light imaging device being disposed to cause an amount of misalignment between a fluorescence image formation position and a visible light image formation position caused by the image-formation optical system to correspond to a difference between an optical path length of fluorescence and an optical path length of visible light, the fluorescence and the visible light forming the respective images via the color-separation-prism optical system, and, where a focal length of the image-formation optical system is represented by f [mm], and an air-equivalent optical path length from the image-formation optical system to an imaging device is represented by Fb [mm], the image-formation optical system has the focal length and the air-equivalent optical path length that satisfy a condition represented by the following expression (1), $$Fb/f > 0.72 \qquad \text{expression (1).}$$

Further, according to the present disclosure, there is provided an imaging apparatus including a rigid-scope optical system, the rigid-scope optical system including an image-formation optical system that causes an image in each of wavelength bands to be formed in a predetermined imaging device, the wavelength bands including a fluorescence wavelength band belonging to a near-infrared light wavelength band and a visible light wavelength band, a color-separation-prism optical system having a dichroic film that separates an optical path of light to be imaged by the image-formation optical system into an optical path of the visible light wavelength band and an optical path of the fluorescence wavelength band, a visible light imaging device that forms an image of the visible light wavelength band, and a fluorescence imaging device that forms an image in the fluorescence wavelength band, in which the visible light imaging device and the fluorescence imaging device are disposed to cause an optical path difference between an optical path length of a visible light wavelength band and an optical path length of a fluorescence wavelength band to correspond to an amount of misalignment between a fluorescence image formation position and a visible light image formation position caused by the image-formation optical system, the visible light forming an image in the visible light imaging device via the color-separation-prism optical system, the fluorescence forming an image in the fluorescence imaging device via the color-separation-prism optical system, and, where a focal length of the image-formation optical system is represented by f [mm], and an air-equivalent optical path length from the image-formation optical system to an imaging device is represented by Fb [mm], the image-formation optical system has the focal length and the air-equivalent optical path length that satisfy a condition represented by the following expression (1), $$Fb/f > 0.72 \qquad \text{expression (1).}$$

Further, according to the present disclosure, there is provided an endoscope unit including: a rigid-scope unit that generates an image of a predetermined imaging target of a fluorescence wavelength band belonging to a near-infrared light wavelength band and an image of the predetermined imaging target of a visible light wavelength band; an imaging unit that includes a rigid-scope optical system coupled to the rigid-scope unit, a visible light imaging device in which the image of the visible light wavelength band is formed, and a fluorescence imaging device in which the image of the fluorescence wavelength band is formed, and generates a captured picture image of the imaging target of the fluorescence wavelength band and a captured picture image of the imaging target of the visible light wavelength band, in which the rigid-scope optical system includes an image-formation optical system that causes an image in each of the fluorescence wavelength band and the visible light wavelength band to be formed in a predetermined imaging device, and a color-separation-prism optical system having a dichroic film that separates an optical path of light to be imaged by the image-formation optical system into an optical path of the visible light wavelength band and an optical path of the fluorescence wavelength band, the visible light imaging device and the fluorescence imaging device are disposed to cause an optical path difference between an optical path length of a visible light wavelength band and an optical path length of a fluorescence wavelength band to correspond to an amount of misalignment between a fluorescence image formation position and a visible light image formation position caused by the image-formation optical system, the visible light forming an image in the visible light imaging device via the color-separation-prism optical system, the fluorescence forming an image in the fluorescence imaging device via the color-separation-prism optical system, and, where a focal length of the image-formation optical system is represented by f [mm], and an air-equivalent optical path length from the image-formation optical system to an imaging device is represented by Fb [mm], the image-formation optical system has the focal length and the air-equivalent optical path length that satisfy a condition represented by the following expression (1), $$Fb/f > 0.72 \qquad \text{expression (1).}$$

According to the present disclosure, the image-formation optical system causes the respective images to be formed in the fluorescence imaging device and the visible light imaging device, the fluorescence imaging device and the visible light imaging device being disposed to cause the amount of misalignment between the fluorescence image formation position and the visible light image formation position caused by the image-formation optical system to be in association with the difference between the optical path length of the fluorescence and the optical path length of the visible light, the fluorescence and the visible light forming the respective images via the color-separation-prism optical system, and the image-formation optical system satisfies the condition represented by the expression (1)

Effects of the Invention

As described above, according to the present disclosure, it is possible to achieve reduction in size while ensuring reliability as an apparatus, and to achieve further resolution of a captured picture image to be obtained.

It is to be noted that the effects described above are not necessarily limitative. With or in the place of the above effects, there may be achieved any one of the effects described in this specification or other effects that may be grasped from this specification.

BRIEF DESCRIPTION OF DRAWINGS

FIG. 2B is an explanatory diagram schematically illustrating the color-separating-prism optical system included in the rigid-scope optical system according to the embodiment.

FIG. 8A is a graph indicating a simulation result of longitudinal aberration of the image-formation optical system of Example 1.

FIG. 9B is a graph indicating a simulation result of lateral aberration of the image-formation optical system of Example 2.

FIG. 11B is a graph indicating a simulation result of lateral aberration of the image-formation optical system of Example 4.

MODES FOR CARRYING OUT THE INVENTION

The following describes a preferred embodiment of the present disclosure in detail with reference to the accompanying drawings. It is to be noted that, in this description and the accompanying drawings, components that have substantially the same functional configuration are indicated by the same reference signs, and thus redundant description thereof is omitted.

It is to be noted that description is given in the following order.
1. Embodiment
   1.1. Regarding Rigid-Scope Optical System
   1.2. Regarding Imaging Apparatus
   1.3. Regarding Endoscope System
2. Examples Embodiment

Figure 1:
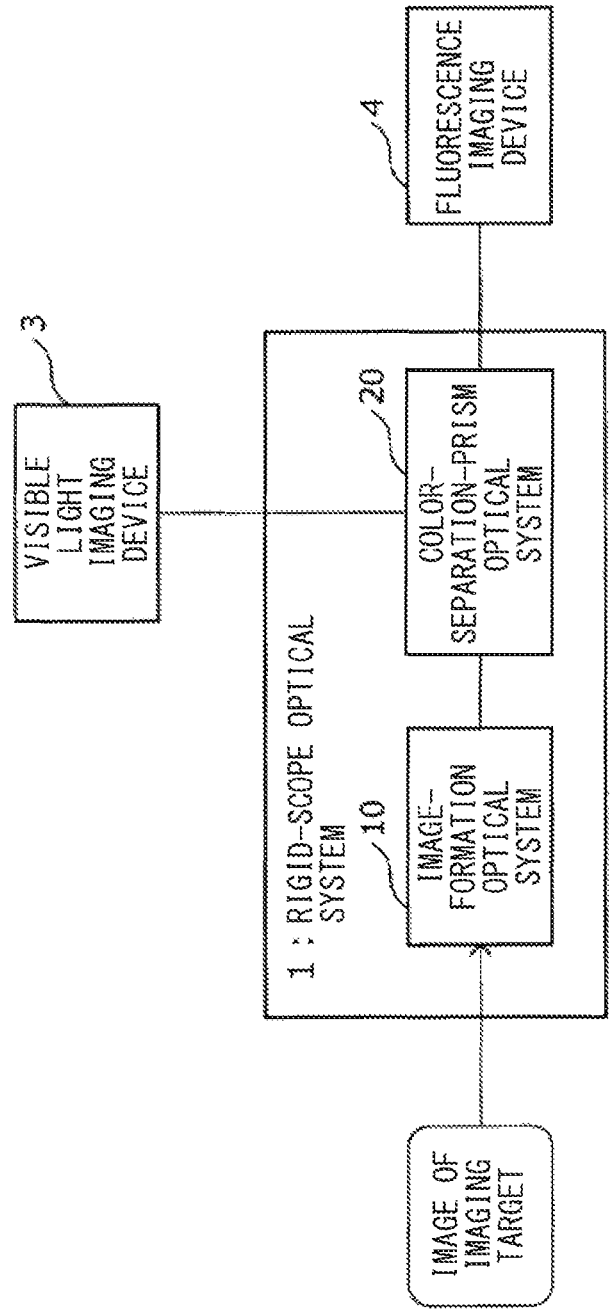
FIG. 1 is an explanatory diagram schematically illustrating an overall configuration of a rigid-scope optical system according to an embodiment of the present disclosure.
Figure 2A:
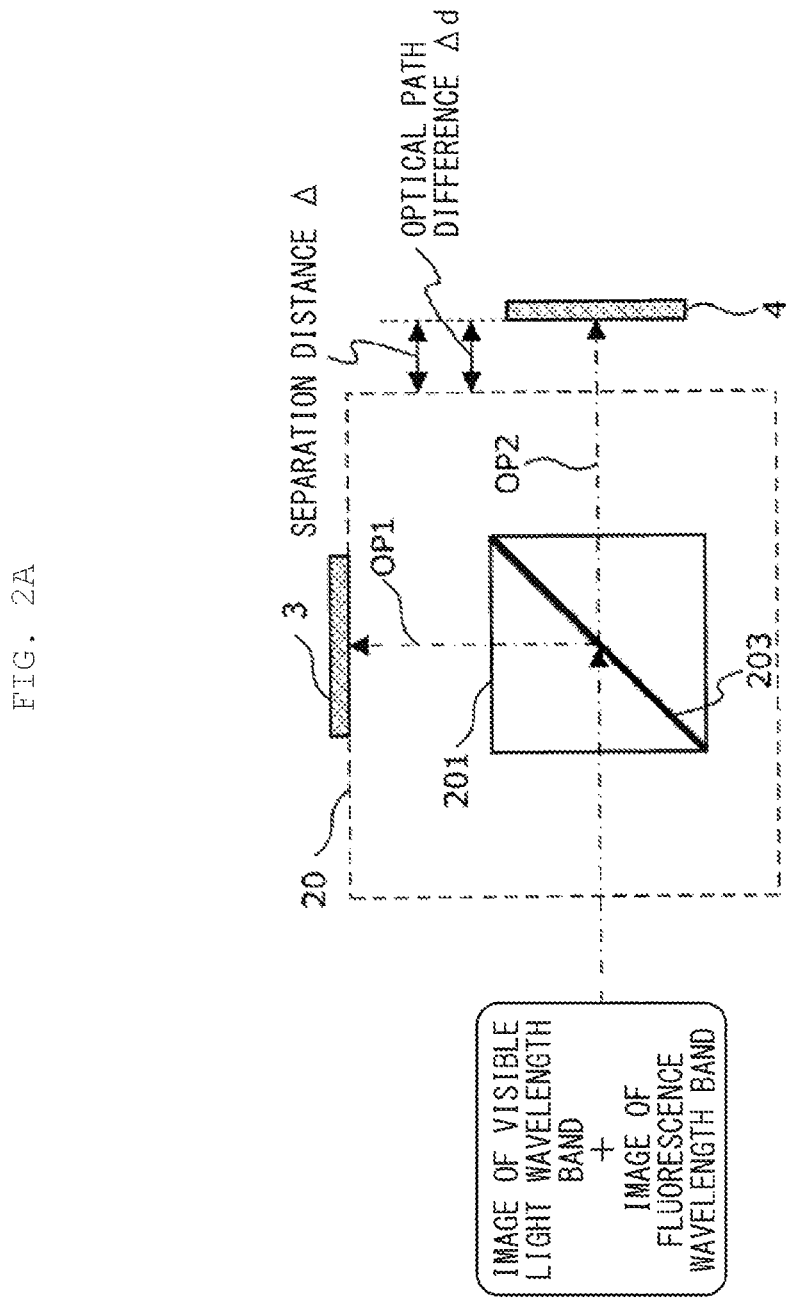
FIG. 2A is an explanatory diagram schematically illustrating a color-separating-prism optical system included in the rigid-scope optical system according to the embodiment.
Figure 3:
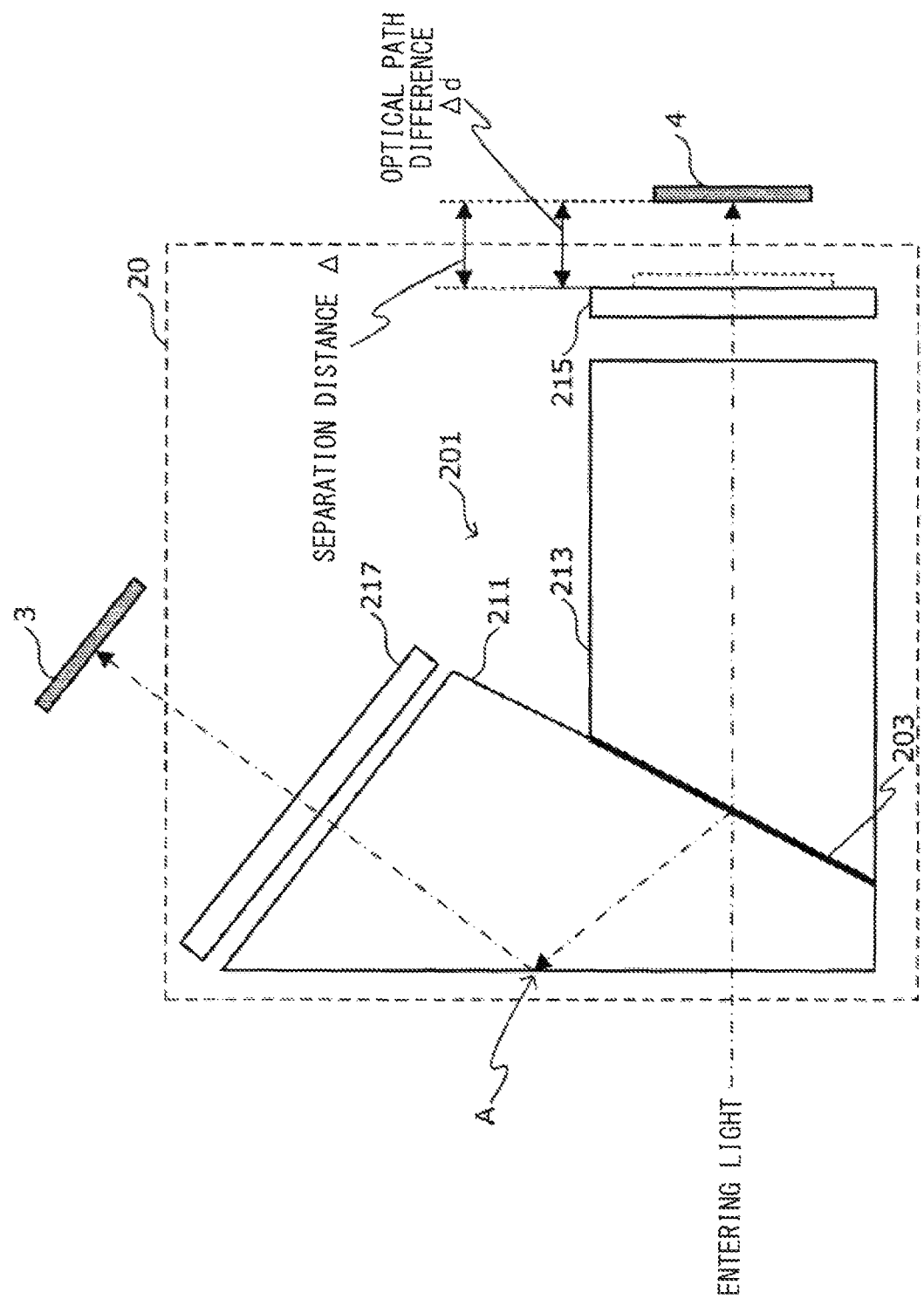
FIG. 3 is an explanatory diagram schematically illustrating the color-separating-prism optical system included in the rigid-scope optical system according to the embodiment.
Figure 4:
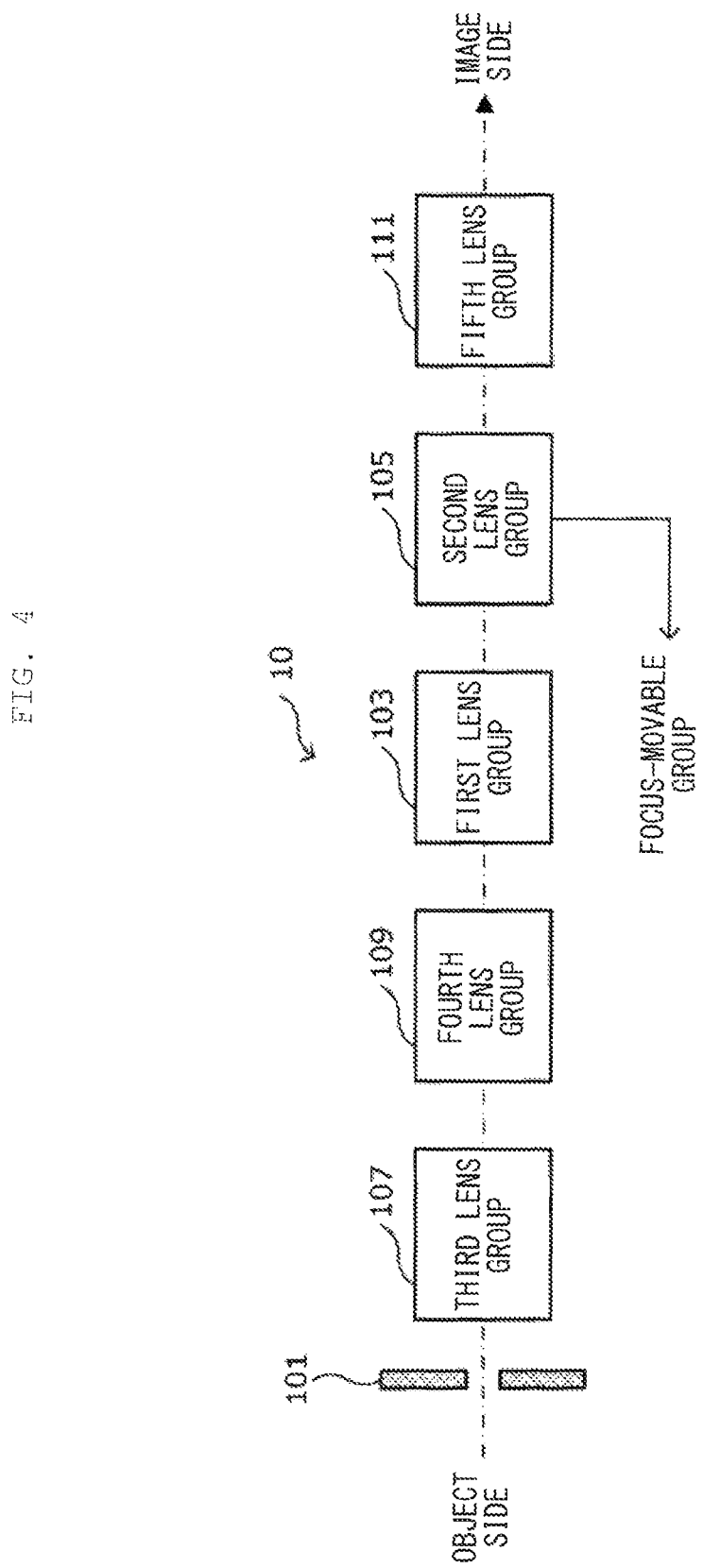
FIG. 4 is an explanatory diagram schematically illustrating a configuration of an image-formation optical system included in the rigid-scope optical system according to the embodiment.

[Regarding Rigid-Scope Optical System]
First, referring to FIGS. 1 to 4, a rigid-scope optical system according to a first embodiment of the present disclosure will be described in detail. FIG. 1 is an explanatory diagram schematically illustrating an overall configuration of the rigid-scope optical system according to the present embodiment. FIGS. 2A to 3 are each an explanatory diagram schematically illustrating a color-separating-prism optical system included in the rigid-scope optical system according to the present embodiment. FIG. 4 is an explanatory diagram schematically illustrating a configuration of an image-formation optical system included in the rigid-scope optical system according to the present embodiment.

The rigid-scope optical system according to the present embodiment is an optical system used for imaging an image obtained by a rigid scope, also called a rigid endoscope.

First, referring to FIG. 1, an overall configuration of a rigid-scope optical system 1 according to the present embodiment will be briefly described below.

[Regarding Overall Configuration]

The rigid-scope optical system 1 according to the present embodiment includes, as schematically illustrated in FIG. 1, an image-formation optical system 10, and a color-separation-prism optical system 20. Further, outside the rigid-scope optical system 1, a visible light imaging device 3 and a fluorescence imaging device 4 are provided.

The visible light imaging device 3 is provided on an optical path of a visible light wavelength band branched by the color-separation-prism optical system 20, and forms an image including light belonging to the visible light wavelength band, out of an image of an imaging target. The fluorescence imaging device 4 is provided on an optical path of a fluorescence wavelength band branched by the color-separation-prism optical system 20, and an image including light belonging to the fluorescence wavelength band is formed, out of the image of the imaging target. The visible light imaging device 3 and the fluorescence imaging device 4 are not particularly limited, and various known CCD sensors, CMOS sensors, and the like may be used therefor.

For example, the visible light imaging device 3 is preferably a CMOS sensor or a CCD sensor using a Bayer array color filter or another color filter having high color reproducibility of visible light. Further, the fluorescence imaging device 4 is preferably a CMOS sensor or a CCD sensor which does not use a color filter, for example, because it is preferable to use the maximum sensitivity of the sensor for near-infrared ray imaging.

The image-formation optical system 10 is an optical system for causing images of the imaging target (specifically, an image in the visible light wavelength band and an image in the fluorescence wavelength band belonging to the near-infrared wavelength band) to be each formed in the corresponding imaging device. The image-formation optical system 10 according to the present embodiment has a lens configuration as described in detail below, thereby being corrected in axial chromatic aberration and exhibiting an excellent optical characteristic in each of the fluorescence wavelength band and the visible light wavelength band. Such an image-formation optical system 10 is described in more detail below.

The color-separation-prism optical system 20 is an optical system that separates an optical path of light to be image by the image-formation optical system 10 into an optical path of the visible light wavelength band and an optical path of the fluorescence wavelength band. The color-separation-prism optical system 20 according to the present embodiment includes at least a dichroic film that separates light into light belonging to the visible light wavelength band and light belonging to the fluorescence wavelength band, and such a dichroic film separates the optical path of the light to be imaged by the image-formation optical system 10 into the two optical paths. Such a color-separation-prism optical system 20 is also described in detail below.

[Regarding Color-Separation-Prism Optical System 20]

Next, the color-separation-prism optical system 20 according to the present embodiment will be described referring to FIGS. 2A to 3.

The color-separation-prism optical system 20 according to the present embodiment is an optical system incorporated in the rigid-scope optical system 1 according to the present embodiment for satisfying a desired specification.

For simultaneously imaging a visible light ray and a near-infrared ray (fluorescence) with high image quality (e.g., 4K resolution or higher), it is important to spectrally separate light into the visible light ray and the near-infrared ray and perform imaging with respective individual imaging devices corresponding to the visible light ray and the near-infrared ray. Therefore, the rigid-scope optical system 1 according to the present embodiment is provided with a prism optical system including a predetermined dichroic film as the color-separation-prism optical system 20, thereby separating the optical path of the light to be imaged by the image-formation optical system 10 into the optical path of the visible light wavelength band and the optical path of the fluorescence wavelength band.

Such a color-separation-prism optical system 20 includes, for example, as schematically illustrated in the FIG. 2A, at least a color-separation prism 201, and a dichroic film 203 having a predetermined optical characteristic is provided inside the color-separation prism 201. The dichroic film 203 has an optical characteristic in which, for example, in a case where the imaging devices are disposed as illustrated in FIG. 2A, light belonging to the visible light wavelength band is reflected and light belonging to the near-infrared wavelength band (fluorescence wavelength band) is transmitted. In contrast, in a case where the positions of the visible light imaging device 3 and the fluorescence imaging device 4 are inverse to those illustrated in FIG. 2A, a dichroic film 203 having an optical characteristic in which the light belonging to the visible light wavelength band is transmitted and the light belonging to the near-infrared wavelength band (fluorescence wavelength band) is reflected is used.

The light to be imaged by the image-formation optical system 10 enters the color-separation prism 201 including the dichroic film 203 as described above, and thus, the optical path of the light is branched into an optical path OP1 of the visible light wavelength band and an optical path OP2 of the fluorescence wavelength band.

Further, an infrared cut filter or the like (not illustrated) is preferably provided on an optical axis of the optical path OP1 of the visible light wavelength band, for removing near-infrared light (fluorescence) that may leak into the optical path OP1 of the visible light wavelength band. The provision of such an infrared cut filter makes it possible to further improve color reproducibility of a visible light picture image generated by the visible light imaging device 3. Similarly, a narrow-band bandpass filter (not illustrated) that transmits light in the fluorescence wavelength band of interest is preferably provided on an optical axis of the optical path OP2 of the fluorescence wavelength band, for removing excitation light and visible light that may leak into the optical path OP2 of the fluorescence wavelength band. This makes it possible to further improve contrast of a fluorescence picture image generated by the fluorescence imaging device 4.

Further, in the image-formation optical system 10 according to the present embodiment, imaging positions of the visible light ray and the near-infrared ray are different from each other due to axial chromatic aberration. Thus, in FIG. 2A, for example, even if the fluorescence imaging device 4 is provided at a position optically conjugate with the visible light imaging device 3, a situation arises in which the image is in focus in the visible light imaging device 3 while the image is not in focus in the fluorescence imaging device 4. However, the rigid-scope optical system 1 according to the present embodiment is able to easily correct such axial chromatic aberration by branching the optical path into two by the color-separation-prism optical system 20 and providing two types of imaging devices.

For example, as schematically illustrated in FIG. 2A, an amount of focus misalignment between the visible light ray and the near-infrared ray is grasped in advance, and the visible light imaging device 3 is fixed in advance at a position where the visible light ray is in focus. Then, the fluorescence imaging device 4 may be fixed and installed at a position separated from the position conjugate with the visible light imaging device 3 by a separation distance A, so that the identified amount of misalignment corresponds to an optical path difference between an optical path length of the optical path OP1 of the visible light wavelength band and an optical path length of the optical path OP2 of the fluorescence wavelength band.

Further, for example, as schematically illustrated in FIG. 2B, the visible light imaging device 3 is fixed in advance at a position where the visible light ray is in focus, and the fluorescence imaging device 4 is mounted to allow the installation position to be variable. Then, a fluorescence picture image focusing mechanism 30 such as an actuator is provided, which varies a separation distance A between: the color-separation-prism optical system 20 and the visible light imaging device 3; and the fluorescence imaging device 4. In such a case, the fluorescence picture image focusing mechanism 30 varies a relative positional relationship between: the fluorescence imaging device 4; and the color-separation-prism optical system 20 and the visible light imaging device 3, thereby making it possible to easily correct the axial chromatic aberration caused by the image-formation optical system 10.

It is to be noted that, according to the method illustrated in FIG. 2B, for example, even in a case where a fluorescence emission position of the ICG reagent introduced into the inside of a viscera exists on back side of a surface of the viscera, it is possible to make a situation in which the surface of the viscera is observed in the visible light ray and the fluorescence emission position of the inside of the viscera is observed in the near-infrared ray.

As the color-separation-prism optical system 20 having a function as described above, it is preferable to use the color-separation-prism optical system 20 like the one disclosed in PTL 2, for example, which is schematically illustrated in FIG. 3.

In the color-separation-prism optical system 20 illustrated in FIG. 3, the color-separation prism 201 is a prism in which a first prism 211 and a second prism 213 are bonded to each other, and the first prism 211 and the second prism 213 are bonded to each other via the dichroic film 203. That is, the dichroic film 203 is provided at an interface between the first prism 211 and the second prism 213.

The first prism 211 is a prism that functions as an optical path of the visible light wavelength band through which light belonging to the visible light wavelength band and light belonging to the fluorescence wavelength band (i.e., entering light) enter and the light belonging to the visible light wavelength band is guided. Further, the second prism 213 is a prism which functions as an optical path of the fluorescence wavelength band through which the light belonging to the fluorescence wavelength band is guided.

The light entering the first prism 211 travels straight in the first prism 211, and the light belonging to the visible light wavelength band and the light belonging to the fluorescence wavelength band are separated from each other by the dichroic film 203 obliquely provided on the optical axis.

The light belonging to the visible light wavelength band is reflected by the dichroic film 203 and guided inside the first prism 211. Here, the reflected and separated light belonging to the visible light wavelength band (i.e., the visible light ray) is totally reflected once at a position A illustrated in FIG. 3, and is transmitted to the outside of the first prism 211. Thus, it is possible to make the angle of a dichroic film 203-formed surface with respect to the optical axis close to perpendicular. Conversely, the angle at which dichroic film 203 according to the present embodiment is installed on the optical axis is set to cause a total reflection condition of the visible light ray at the position A to be satisfied. The placement of the dichroic film 203 in this way makes it possible to suppress variation in a spectral characteristic of the dichroic film 203 due to difference in an angle of incidence between an upper light beam and a lower light beam, even in a case where light beams each having a bright F-value enter the first prism 211, and to accurately perform wavelength separation.

The visible light ray transmitted through the first prism 211 is guided to the visible light imaging device 3. In this case, an infrared cut filter 217 may be provided between an exit surface of the first prism 211 and the visible light imaging device 3. As such an infrared cut filter 113, for example, it is possible to use a known absorbing filter or the like such as C5000 manufactured by HOYA Corporation.

In contrast, the light belonging to the fluorescence wavelength band transmitted through the dichroic film 203 enters the second prism 213 and travels straight inside the second prism 213. An end surface of the second prism 213 on side opposite to side on which the dichroic film 203 is provided (in other words, an exit surface of the second prism 213 on downstream side of the optical axis) to be perpendicular to the optical axis, and the light belonging to the fluorescence wavelength band is transmitted to the outside of the second prism 213 while maintaining a state of being perpendicular to the exit surface of the second prism 213.

The light belonging to the fluorescence wavelength band transmitted through the second prism 213 enters a narrow-band bandpass filter 215 provided at a subsequent stage.

The preferred mode as color-separation prism 201 according to the present embodiment has been described above in detail. It is to be noted that a material of the color-separation prism 201 according to the present embodiment is not particularly limited, and it is possible to use appropriately known optical glass or optical crystal depending on a wavelength of light guided inside the color-separation prism 201.

Here, the respective optical characteristics of the dichroic film 203 and the narrow-band bandpass filter 215 as illustrated in FIG. 3 will be specifically described below focusing on the use of ICG as a fluorescent reagent.

The ICG has an excitation wavelength of approximately 769 nm, and when the ICG is excited by excitation light having such an excitation wavelength, fluorescent light belonging to the near-infrared wavelength band having a wavelength of 832 nm is generated, for example.

In such a case, if the placement of the imaging device as illustrated in FIG. 3 is achieved, it is preferable that the optical characteristic (specifically, a spectral transmittance) of the dichroic film 203 have a transmittance of 90% or more in a wavelength band of 780 nm to 880 nm, and have a transmittance of 10% or less in a wavelength band of 400 nm to 720 nm.

In a case where the transmittance is less than 90% in the wavelength band of 780 nm to 880 nm, a percentage of the fluorescence that is not able to transmit the dichroic film 203 increases and the brightness of the fluorescence picture image decreases, which is not preferable. In addition, in such a case, the fluorescence leaks into the visible light imaging device 3, which lowers the contrast of the visible light picture image, which is not preferable from a viewpoint of image quality of the visible light picture image.

Further, in a case where the transmittance exceeds 10% in the wavelength band of 400 nm to 720 nm, a percentage of the visible light which is not reflected by the dichroic film 203 and is transmitted is increased, and the brightness of the visible light picture image is lowered, which is not preferable. In addition, in such a case, the visible light leaks into the fluorescence imaging device 4, which lowers the contrast of the fluorescence picture image, which is not preferable from a viewpoint of image quality of the fluorescence picture image.

As is clear from the above explanation, the dichroic film 203 according to the present embodiment separates the entering light into two colors: light belonging to a predetermined fluorescence wavelength band a band of a longer wavelength band than the predetermined fluorescence wavelength band; and light belonging to a shorter wavelength band than a predetermined fluorescence wavelength band. For example, the dichroic film 203 having the above-described spectral transmittance is a film that functions as a low-pass filter that separates the entering light into two groups with a boundary of 750 nm, which serves as a boundary between the visible light wavelength band and the fluorescence wavelength band as a boundary.

For example, the optical characteristic (spectral characteristic) of the dichroic film 203 as described above is relatively broad, and when the dichroic film 203 is achieved as an optical multilayered film, it is possible to suppress the number of film layers to approximately several tens of layers, and also to use a common vacuum evaporation method as a manufacturing method.

Further, it is also important that the narrow-band bandpass filter 215 provided in the preceding stage of the fluorescence imaging device 4 be a filter having a bandpass property that reflects light in a wavelength band other than the fluorescence wavelength band and transmits only light in the fluorescence wavelength band light.

In a case of focusing on the fluorescence emitted from ICG belonging to the near-infrared band of a wavelength of 832 nm, it is preferable that the spectral transmittance of the narrow-band bandpass filter 215 have a transmittance of 90% or more in a wavelength band of 820 nm to 850 nm, and a transmittance of 10% or less in a wavelength band of 400 nm to 805 nm and in a wavelength band of 860 nm to 1000 nm.

In a case where the transmittance is less than 90% in the wavelength band of 820 nm to 850 nm, the percentage of the fluorescence that transmits through the narrow-band bandpass filter 215 is reduced, and this decreases the brightness of the fluorescence picture image, which is not preferable. Further, in a case where the transmittance exceeds 10% in the wavelength band of 400 nm to 805 nm and the wavelength band of 860 nm to 1000 nm, external light other than the fluorescence, such as excitation light having a wavelength around 800 nm, is reflected on the fluorescence imaging device 4, and the contrast of the fluorescence picture image is remarkably lowered, which is not preferable.

Further, if the wavelength band of the light transmitted by the narrow-band bandpass filter 215 is wider than the wavelength band from 820 nm to 850 nm, the near-infrared wavelength band contributing to forming the fluorescence picture image becomes too wide. As a result, even if it is possible to correct the center of gravity of axial chromatic aberration by a separation distance A, which will be described later, components having longer wavelength makes the image blurred and the contrast is lowered, which is not preferable.

In addition, if the wavelength band of the light transmitted by the narrow-band bandpass filter 215 is narrower than the wavelength band from 820 nm to 850 nm, the light transmitted through the narrow-band bandpass filter 215 approaches a monochromatic color, which enhances effects of correction of the axial chromatic aberration by the separation distance A, which will be described later, but lowers brightness of the fluorescence picture image, which is not preferable.

The narrow-band bandpass filter 215 according to the present embodiment is manufacturable by using a known optical material depending on the wavelength of the fluorescence of interest. For example, the narrow-band bandpass filter 215 may be manufactured by forming an optical multilayer film on a glass substrate corresponding to BK7, or may be manufactured by forming an optical multilayer film on such a substrate using a visible absorption glass such as R80 manufactured by HOYA Corporation as a substrate. This makes it possible to suppress transmittance of a visible light region and to contribute to improvement in the contrast of the fluorescence picture image, compared to a structure using the glass substrate.

It is to be noted that such a narrow-band bandpass filter 215 is formable by a vacuum evaporation method similarly to the dichroic film 203, but has a spectral characteristic of a narrow band and a sharp rising and falling shape; therefore, the number of film layers is larger than the number of film layers of the dichroic film 203, and is approximately several hundreds of layers. For this reason, it is preferable to employ a film forming method such as an ion beam sputtering method that ensures high reliability than the vacuum evaporation method.

Further, the narrow-band bandpass filter 215 is preferably provided on the optical path OP2 of the fluorescence wavelength band so as to have an entrance surface perpendicular to the optical axis. This makes it possible to suppress variation in the spectral characteristic due to difference in an angle of incidence between an upper light beam and a lower light beam, even in a case where light beams having a bright F-value have entered.

The color-separation-prism optical system 20 according to the present embodiment has been described above in detail by referring to FIGS. 3 to 2A.

[Regarding Image-Formation Optical System 10]

Next, referring to FIG. 4, the image-formation optical system 10 according to the present embodiment will be described in detail.

The image-formation optical system 10 according to the present embodiment is, as described above, an optical system for causing an image in each of the wavelength bands of the fluorescence wavelength band belonging to the near-infrared light wavelength band and the visible light wavelength band to be formed in a predetermined imaging device. The image-formation optical system 10 according to the present embodiment has a lens design that satisfies a condition described in detail below, for example; thus, it is possible to achieve a picture image having an extremely excellent resolution higher than or equal to 4K resolution, and it is also possible to achieve reduction in size of the apparatus itself by achieving reduction in size of the optical system itself. In addition, the optical system satisfying the condition described in detail below is configurable using a common glass material having excellent temperature resistance and chemical resistance, which is highly reliable in application to the medical field; thus, it is possible to achieve the optical system having high reliability even in application to the medical field.

Where a focal length of the image-formation optical system 10 is represented by f [mm] and an air-equivalent optical path length from the image-formation optical system to an imaging device is represented by Fb [mm], the image-formation optical system 10 according to the present embodiment has the focal length f and the air-equivalent optical path length Fb that satisfy a condition represented by the following expression (101).

$$Fb/f > 0.72 \qquad \text{Expression (101)}$$

The condition represented by the above expression (101) is a conditional expression related to a back focus of the image-formation optical system 10, taking into account: the image-formation optical system 10; and a size of the color-separation prism 201 (e.g., the color-separation prism 201 in which two prisms are bonded as illustrated in FIG. 3) located at the subsequent stage of the image-formation optical system 10.

In a case where a value represented by Fb/f is 0.72 or less, it is not possible to secure a physical space in which the color-separation prism 201 is installed, taking into account an internal reflection of the prism and the like, which prevents the rigid-scope optical system 1 from achieving high resolution. Further, although an upper limit of the value represented by Fb/f is not specifically defined, if the value represented by Fb/f becomes too large, an outer diameter of the rearmost lens becomes too large and an effective diameter of prism block front side has to be increased. This does not contribute to reduction in size, which is not preferable. From the viewpoint of reduction in size of the rigid-scope optical system 1, it is preferable that the upper limit of Fb/f is 1.00, for example. The value represented by Fb/f is more preferably 0.75 or more and 1.00 or less, and still more preferably 0.80 or more and 0.96 or less.

It is to be noted that, in the rigid-scope optical system 1 according to the present embodiment, two types of air-equivalent optical path lengths are considered, an air-equivalent optical path length to the visible light imaging device 3 and an air-equivalent optical path length to the fluorescence imaging device 4; however, the air-equivalent optical path length to the fluorescence imaging device 4 can be regarded as the air-equivalent optical path length to the visible light imaging device 3+an amount of position misalignment, thus, in the above expression (101), the air-equivalent optical path length to the visible light imaging device 3 may be used as Fb.

It is preferable that the image-formation optical system 10 satisfying the condition related to the back focus as described above include, in order from object side to image side, at least a diaphragm 101, a first lens group 103 having a positive refractive power, and a second lens group 105 having a positive refractive power, as schematically illustrated in FIG. 4, for example.

Hereinafter, although the term "n-th lens group" is frequently used in this description, the lens group handled by such a term includes not only a case where the lens group includes a set of two or more lenses but also a case where the lens group includes one lens. Further, each lens group may include various spherical lenses, may include various aspherical lenses, or may include a combination of spherical lens(es) and aspherical lens(es).

Here, the first lens group 103 preferably includes, in order from the object side to the image side, a lens having a negative refractive power with a concave surface facing the object side, and at least one lens having a positive refractive power. The second lens group 105 is preferably a focus group that performs focusing depending on an object distance.

In a case where the first lens group 103 does not have the lens having the negative refractive power with the concave surface facing the object side on the most object side, it becomes difficult to have telecentricity of the optical system, and it is not possible to achieve long Fb satisfying the above expression (101). Further, in a case where the first lens group 103 is not a combination of the lens having the negative refractive power and the at least one lens having the positive refractive power, it is not possible to achieve a lens group having a positive refractive power in the first lens group 103 as a whole.

In addition, in a case where the second lens group 105 is not a lens group having the positive refractive power as a whole, it is not possible to properly correct coma aberration, and thus, it is not possible to achieve a better resolution, and in a case where the second lens group 105 is not the focus group, the entire optical system has be moved, which makes it difficult to suppress variation in the angle of view.

In this case, it is preferable that the image-formation optical system 10 according to the present embodiment satisfies a condition represented by the following expression (102), where an air-equivalent optical path length from the image-formation optical system 10 to the color-separation-prism optical system 20 is represented by L [mm].

$$1.4 < L/f < 1.8 \qquad \text{Expression (102)}$$

The conditional expression represented by the expression (102) is a conditional expression defining a total length of the image-formation optical system 10. In a case where a value represented by L/f is 1.4 or less, the lenses have to be thinned or the like to secure a size of the color-separation prism 201 located at the subsequent stage of the image-formation optical system 10; thus, not only the manufacturability is lowered, but also it may be difficult to reduce the size of the image-formation optical system 10 while maintaining reliability in the medical field. Further, in a case where it is necessary to reduce the number of lenses, it may be difficult to reduce the size of the image-formation optical system 10 while demanding for high resolution. In contrast, in a case where the value represented by L/f is 1.8 or more, the total length of the image-formation optical system 10 becomes too long, and it may be difficult to reduce the size of the rigid-scope optical system 1. The value represented by L/f is more preferably 1.5 or more and 1.7 or less, and still more preferably 1.55 or more and 1.65 or less.

Further, in the image-formation optical system 10 according to the present embodiment, it is preferable that the second lens group 105 further satisfies a condition represented by the following expression (103), where a focal length of the second lens group 105 is represented by f2 [mm].

$$1.0 < f2/f < 1.4 \qquad \text{Expression (103)}$$

The conditional expression represented by the expression (103) is a conditional expression defining the focal length f2 of a focus lens group achieved by the second lens group 105. In a case where a value represented by f2/f is 1.0 or less, it is possible to shorten a focus stroke, but aberration correction may become unbalanced, which is not preferable from the viewpoint of an optical characteristic achieved by the image-formation optical system 10. In contrast, in a case where the value represented by f2/f is 1.4 or more, the focus stroke may become too large, and it may become difficult to reduce the size of the image-formation optical system 10. The value represented by f2/f is more preferably 1.15 or more and 1.35 or less, and still more preferably 1.2 or more and 1.3 or less.

Further, as schematically illustrated in FIG. 4, the image-formation optical system 10 according to the present embodiment preferably further includes, between the diaphragm 101 and the first lens group 103, in order from the object side to the image side, at least one of a third lens group 107 having a positive refractive power or a fourth lens group 109 having a negative refractive power.

In such a case, it is preferable that the fourth lens group 109 satisfies a condition represented by the following expression (104), where a focal length of the fourth lens group 109 in the image-formation optical system 10 is represented by f4 [mm].

$$-0.80 < f4/f < -0.35 \qquad \text{Expression (104)}$$

The conditional expression represented by the expression (104) is a conditional expression defining a ratio of a power of a concave lens included in the fourth lens group 109 provided for achieving a negative refractive power to an entire power of the image-formation optical system 10. In a case where a value represented by f4/f is −0.35 or more, the power of the concave lens included in the fourth lens group 109 may become too strong, and it may become difficult to achieve the placement of the lens groups as illustrated in FIG. 4. In contrast, in a case where the value represented by f4/f is −0.80 or less, the power of concave lens included in the fourth lens group 109 becomes weak, and it may be difficult to give telecentricity desired for a long back focus. The value represented by f4/f is more preferably −0.60 or more and −0.30 or less, and still more preferably −0.55 or more and −0.40 or less.

Further, in a case where the image-formation optical system 10 includes the third lens group 107 described above, it is preferable that the second lens group 105 further satisfies a relationship represented by the following expression (105), where a curvature radius at an object-side surface of the lens located on most object side in the third lens group 107 is represented by R3 [mm].

$$0.85 < R3/f \qquad \text{Expression (105)}$$

The expression (105) is a conditional expression defining a curvature of the third lens group 107. The curvature of the third lens group 107 is largely related to spherical aberration of the image-formation optical system 10 as a whole, and it is preferable to suppress the spherical aberration as much as possible in the image-formation optical system 10 as a whole. In a case where a value represented by R3/f is 0.85 or less, the spherical aberration of the image-formation optical system 10 as a whole becomes too large, which is not preferable. In contrast, although the upper limit of the value represented by R3/f is not particularly defined, it is preferably set to be less than 2.5. In a case where the value represented by R3/f is 2.5 or more, it may be difficult to select a glass material to satisfy a desired focal length f3 of the third lens group 107.

Further, as schematically illustrated in FIG. 4, the image-formation optical system 10 according to the present embodiment may further include a fifth lens group 111 having a negative refractive power at a subsequent stage (further image side) of the second lens group 105. The additional provision of such a fifth lens group 111 causes the optical system to be telephoto, and makes it possible to reduce the size of the entire optical system without increasing a size of a stroke of a focus.

Further, the image-formation optical system 10 according to the present embodiment preferably satisfies a condition represented by the following expression (106), where a focal length at a fluorescence wavelength of interest of the image-formation optical system 10 is represented by f(NIR) [mm], and a focal length at a visible light wavelength of the image-formation optical system 10 is represented by f(V) [mm].

$$0.0025 < (f(NIR) - f(V))/f(V) < 0.0060 \qquad \text{Expression (106)}$$

The conditional expression represented by the expression (106) is a conditional expression that defines a range of an amount of misalignment (i.e., a range of axial chromatic aberration of the image-formation optical system 10 as a whole) between a focal position of light belonging to the visible light wavelength band and a focal position of light belonging to the near-infrared wavelength band. In a case where the amount of misalignment between the focal positions is 0.0025 or less, it is demanded to correct all chromatic aberration in the entire wavelength band from the visible light wavelength band to the near-infrared wavelength band, and therefore, it may be difficult to select a glass material. Further, attempting to achieve complete chromatic aberration correction causes necessity to select a glass material lacking in reliability in application to the medical field, which is not preferable. In contrast, in a case where the amount of misalignment between the focal positions is 0.0060 or more, chromatic aberration of the visible light wavelength band may be inadequately corrected, which is not preferable. The amount of misalignment between the focus positions is more preferably 0.0030 or more and 0.0055 or less, and still more preferably 0.0040 or more and 0.0050 or less.

It is to be noted that the various lens characteristics of each lens group other than the above are not particularly limited, and may be appropriately set within the above conditional expressions so as to satisfy a desired conditional expression for the image-formation optical system 10 as a whole.

Further, as for the glass material of each lens included in the image-formation optical system 10 according to the present embodiment, it is possible to use any glass material as long as it is a glass material having high reliability in application to the medical field, and it is not particularly limited. However, it is preferable not to use a soft glass material which has large temperature variation and is susceptible to scratches, or a glass material which has a high refractive index, does not easily transmit light of a low wavelength, and has an influence on color reproduction at the time of imaging.

The image-formation optical system 10 according to the present embodiment has been described in detail above.

The rigid-scope optical system 1 according to the present the present embodiment having the above-described configuration is able to achieve reduction in size while ensuring reliability as a device, and to achieve further resolution of a captured picture image to be obtained.

[Regarding Imaging Apparatus]

With the use of the rigid-scope optical system 1 described above, it becomes possible to achieve an imaging apparatus (specifically, a camera head unit (CHU)) applicable to various endoscope systems (e.g., rigid endoscope systems).

[Regarding Endoscope System]

Figure 5:
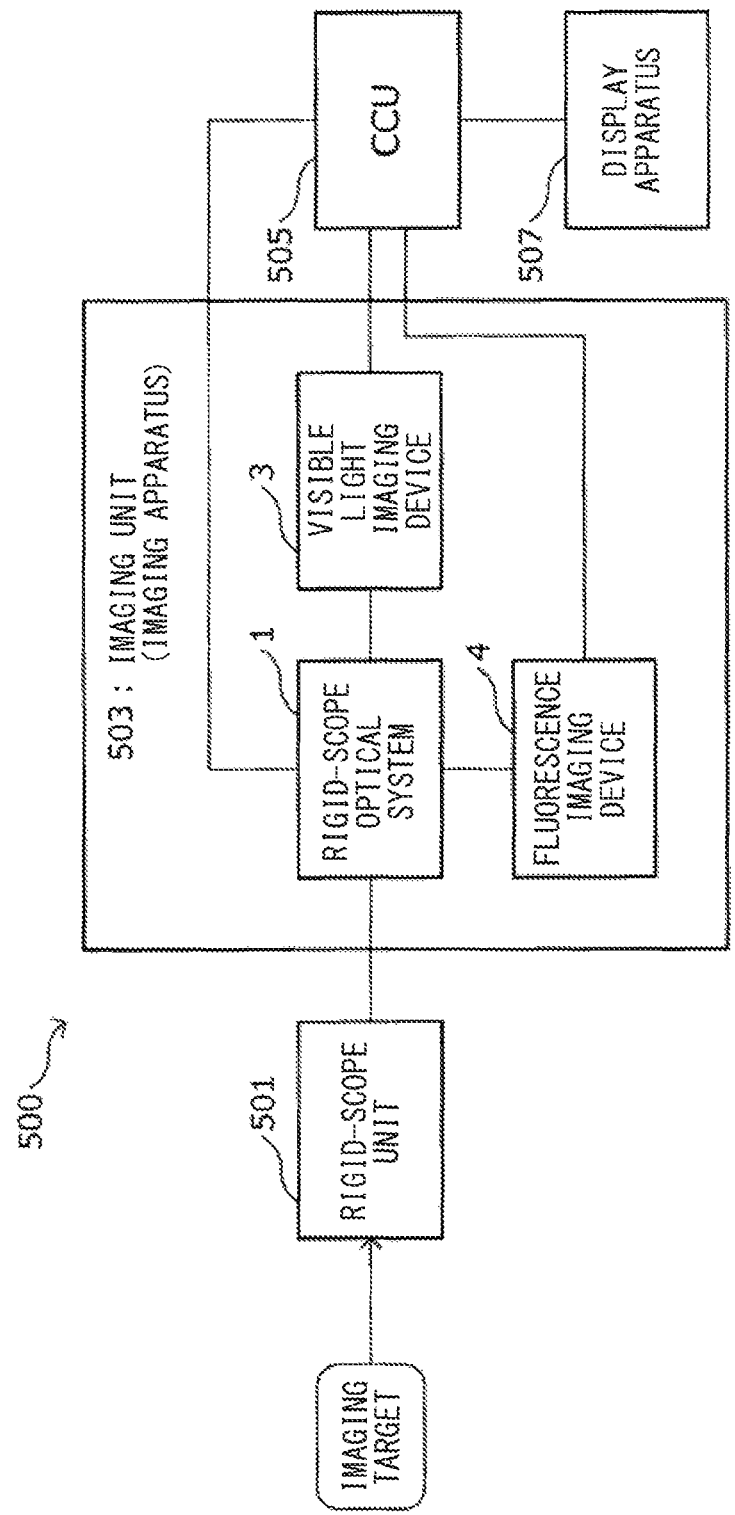
FIG. 5 is an explanatory diagram schematically illustrating an overall configuration of an endoscope system according to the embodiment.
Figure 6:
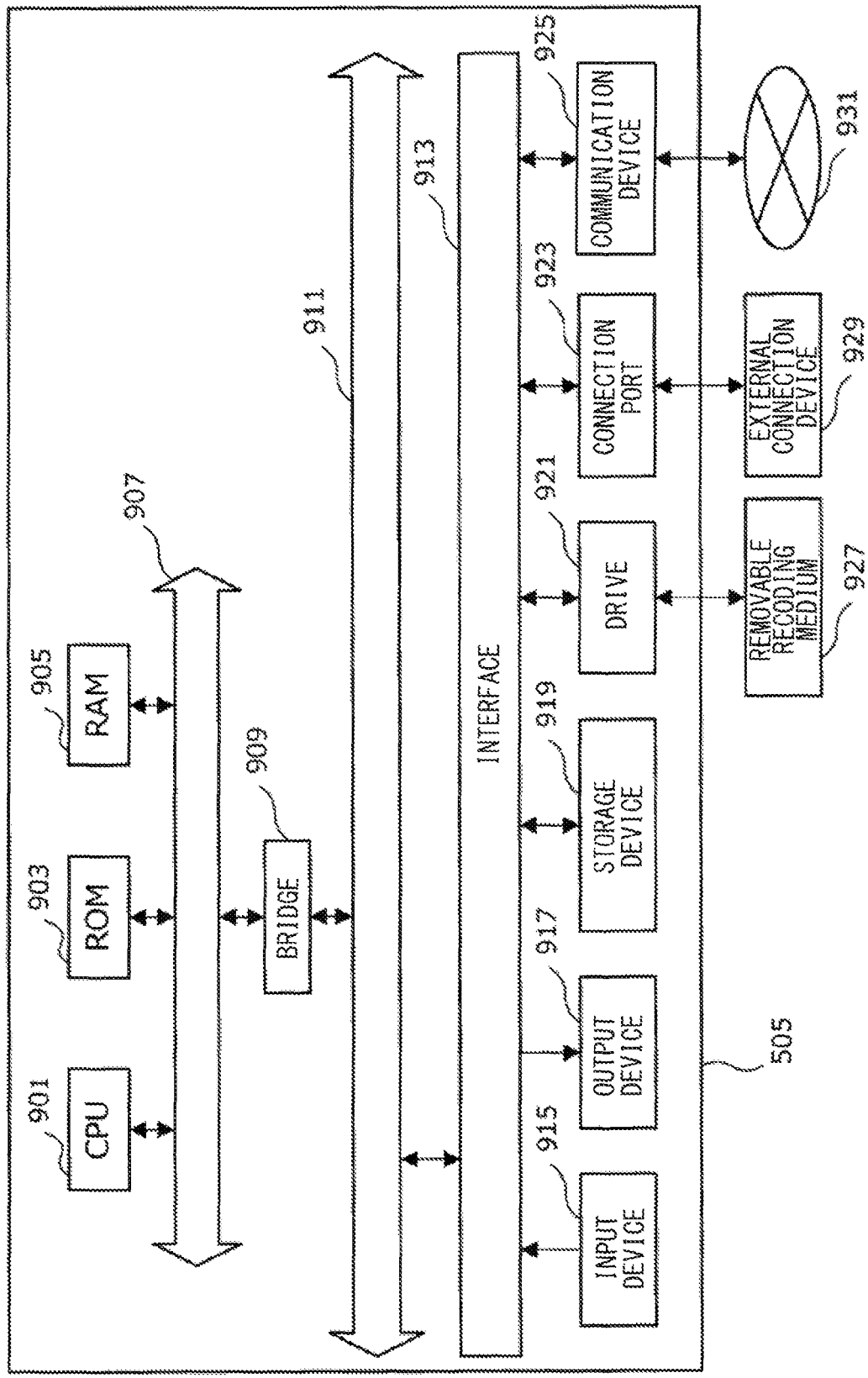
FIG. 6 is a block diagram illustrating an example of a hardware configuration of a CCU included in the endoscope system according to the embodiment.

Next, an endoscope system to which the rigid-scope optical system 1 according to the present embodiment is applied will be briefly described referring to FIGS. 5 and 6. FIG. 5 is an explanatory diagram schematically illustrating an overall configuration of the endoscope system according to the present embodiment, and FIG. 6 is a block diagram illustrating an example of a hardware configuration of CCU included in the endoscope system according to the present embodiment.

As described above, it is possible to construct the endoscope system by combining the rigid-scope optical system 1 (more specifically, the imaging apparatus including the rigid-scope optical system 1) and an endoscope unit (for example, a rigid-scope unit).

As schematically illustrated in FIG. 5, the endoscope system 500 includes at least a rigid-scope unit 501, an imaging unit 503 having the rigid-scope optical system 1, the visible light imaging device 3, and the fluorescence imaging device 4 according to the present embodiment, a camera control unit (CCU) 505 that performs overall control on functions which the imaging unit 503 has, and a display apparatus 507.

Here, owing to the inclusion of the rigid-scope optical system 1 described above, the imaging unit 503 including the rigid-scope optical system 1 has similar effects as those achieved by the rigid-scope optical system 1, thus, the detailed description thereof will be omitted below.

The rigid-scope unit 501 serving as an example of the endoscope unit includes, order from the object side (imaging target side), an objective lens (not illustrated), multiple relay lenses (not illustrated), and an eyepiece (not illustrated). The objective lens forms an aerial image of an imaging target, and the relay lenses performs relay image formation at unity magnification on the formed aerial image multiple times. Thereafter, the eyepiece performs afocal image formation on the last aerial image, which makes it possible to observe the aerial image with the naked eye.

Captured picture images (a visible light picture image and a fluorescence picture image) generated in the imaging unit 503 are outputted to the CCU 505, and the picture images are superimposed by the CCU 505, for example, to generate a superimposed picture image. The captured visible light picture image and fluorescence picture image, and the generated superimposed picture image are displayed on the display apparatus 507 under the control of the CCU 505.

Here, the CCU 505 and the display apparatus 507 are not particularly limited, and it is possible to use appropriately a known CCU and a known display apparatus.

[Regarding Hardware Configuration of CCU 505]

Next, referring to FIG. 6, a hardware configuration of the CCU 505 according to an embodiment of the present disclosure will be described in detail.

The mainly includes a CPU 901, a ROM 903, and a RAM 905. Further, the CCU 505 further includes a host bus 907, a bridge 909, an external bus 911, an interface 913, an input device 915, an output device 917, a storage device 919, a drive 921, a connection port 923, and a communication device 925.

The CPU 901 functions as an arithmetic processing unit and a control unit, and controls an overall operation or a portion of operation in the CCU 505 in accordance with various programs recorded in the ROM 903, the RAM 905, the storage device 919, or a removable recoding medium 927. The ROM 903 stores a program, an arithmetic parameter, or the like to be used by the CPU 901. The RAM 905 primarily stores a program to be used by CPU 901, a parameter that varies appropriately in executing the program, and the like. These are coupled to each other via the host bus 907 including an internal bus such as a CPU bus.

The host bus 907 is coupled via the bridge 909 to the external bus 911 such as a PCI (Peripheral Component Interconnect/Interface) bus.

The input device 915 is a manipulation unit manipulated by a user, such as a mouse, a keyboard, a touch panel, a button, a switch, a lever, and the like. Further, the input device 915 may be, for example, a remote-control unit (a so-called remote controller) using infra-red rays or other radio waves, or may be an external connection device 929 such as a mobile telephone or a PDA compatible with manipulation of the CCU 505. Further, the input device 915 includes, for example, an input control circuit that generates an input signal on the basis of information inputted by the user using the above-described manipulation unit, and outputs the input signal to the CPU 901. The user of the CCU 505 is able to input various types of data to the CCU 505 or provide the CCU 505 with an instruction on a processing operation by manipulating the input device 915.

The output device 917 includes a device that is able to visually or audibly notifying the user of acquired information. Examples of such a device include a display device such as a CRT display device, a liquid crystal display device, a plasma display device, an EL display device, and a lamp, an audio output device such as a speaker or headphones, a printer device, a mobile phone, a facsimile, and the like. The output device 917 outputs, for example, a result obtained by various processes performed by the CCU 505. Specifically, the display device displays the result obtained by the various processes performed by the CCU 505 as text or an image. Meanwhile, the audio output device converts an audio signal including reproduced audio data, acoustic data, and the like into an analog signal, and outputs the analog signal.

The storage device 919 is a device for storing data configured as an example of a storage of the CCU 505. The storage device 919 includes, for example, a magnetic storage device such as an HDD (Hard Disk Drive), a semiconductor storage device, an optical storage device, a magneto-optical storage device, or the like. The storage device 919 stores a program to be executed by the CPU 901, various data, and various data acquired from the outside.

The drive 921 is a reader/writer for a recording medium, and is built in or externally attached to the CCU 505. The drive 921 reads information recorded on the removable recoding medium 927 such as a magnetic disk, an optical disc, a magneto-optical disk, or a semiconductor memory, and outputs the read information to the RAM 905. In addition, the drive 921 is also able to write a record to the removable recoding medium 927 such as the magnetic disk, the optical disc, the magneto-optical disk, or the semiconductor memory that is mounted on the drive 921. The removable recoding medium 927 may be, for example, a DVD medium, an HD-DVD medium, a Blu-ray (registered trademark) medium, etc. Further, the removable recoding medium 927 may be compact flash (registered trademark) (CompactFlash: CF), a flash memory, an SD memory card (Secure Digital memory card), or the like. The removable recoding medium 927 may be, for example, an IC card (Integrated Circuit card) on which a non-contact type IC chip is mounted, an electronic device, or the like.

The connection port 923 is used to couple a device directly to the CCU 505. Examples of the connection port 923 include a USB (Universal Serial Bus) port, an IEEE1394 port, an SCSI (Small Computer System Interface) port, and the like. Other examples of the connection port 923 include an RS-232C port, an optical audio terminal, an HDMI (High-Definition Multimedia Interface) port, and the like. By coupling the external connection device 929 to the connection port 923, the CCU 505 acquires various types of data directly from the external connection device 929 or provide the external connection device 929 with various types of data.

The communication device 925 is, for example, a communication interface including a communication device to be coupled to a communication network 931. The communication device 925 may be, for example, a communication card or the like for a wired or wireless LAN (Local Area Network), Bluetooth (registered trademark), or WUSB (Wireless USB). Further, the communication device 925 may be a router for optical communication, a router for ADSL (Asymmetric Digital Subscriber Line), or a modem for various types of communication. The communication device 925 is able to transmit and receive a signal and the like to and from the Internet or another communication device in accordance with a predetermined protocol such as TCP/IP, for example. Further, the communication network 931 to be coupled to the communication device 925 includes a network or the like coupled via wire or radio, and may be, for example, the Internet, a home LAN, infrared communication, radio wave communication, satellite communication, or the like.

An example of the hardware configuration that is able to achieve the functions of the CCU 505 according to an embodiment of the present disclosure has been described above. Each of the components described above may be configured using a general-purpose member, or may be configured by hardware specialized for the function of each component. Accordingly, the hardware configuration to be used is changeable as appropriate in accordance with the technical level at the time of carrying out the present embodiment.

Referring to FIGS. 5 and 6, the endoscope system 500 using the rigid-scope optical system 1 according to the present embodiment has been described briefly.

EXAMPLES

Hereinafter, the image-formation optical system included in the rigid-scope optical system according to the present disclosure will be specifically described with reference to the following Examples. It is to be noted that the following Examples are merely examples of the image-formation optical system included in the rigid-scope optical system according to the present disclosure, and the image-formation optical system according to the present disclosure is not limited to the examples indicated below.

Figure 7A:
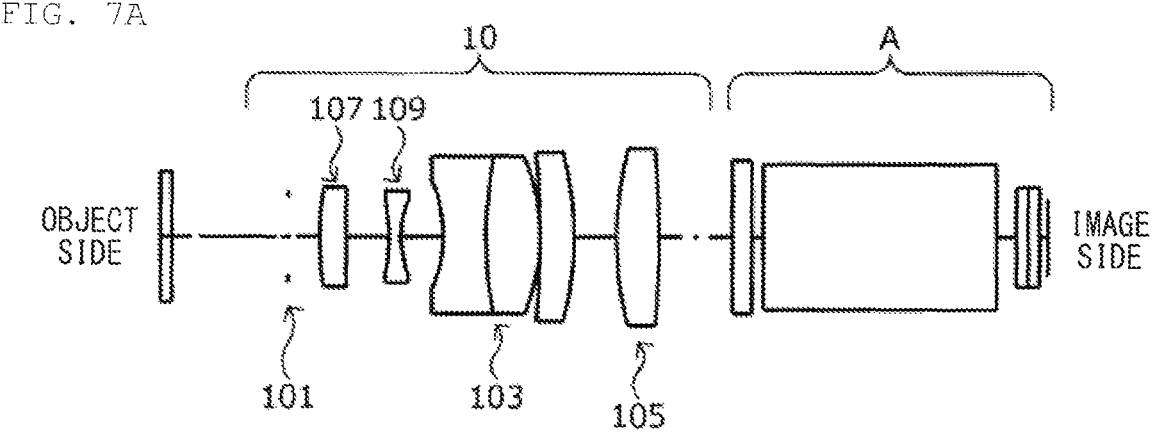
FIG. 7A is a schematic view of a configuration of an image-formation optical system of Example 1.
Figure 7B:
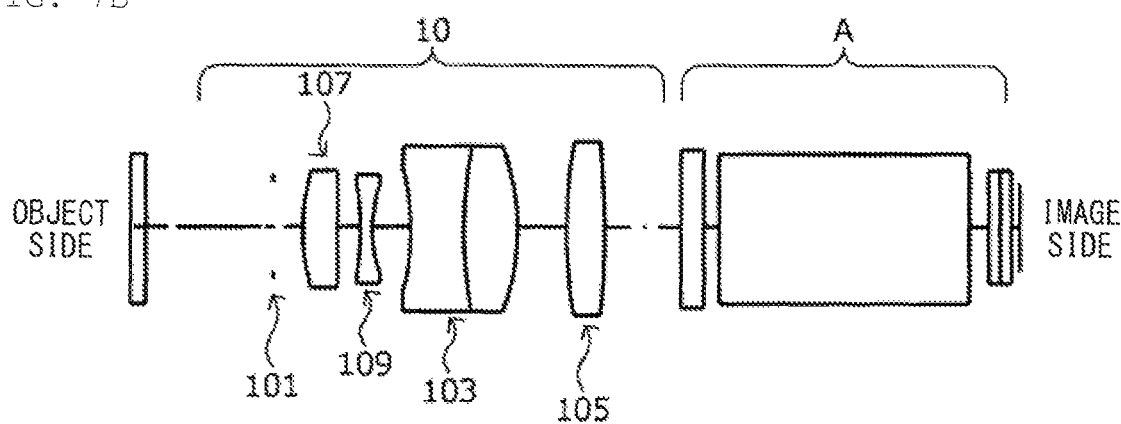
FIG. 7B is a schematic view of a configuration of an image-formation optical system of Example 2.
Figure 7C:
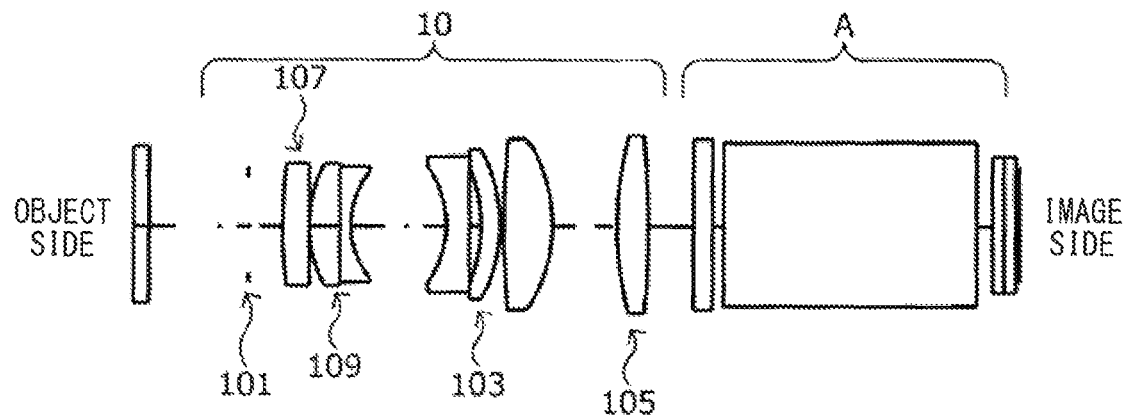
FIG. 7C is a schematic view of a configuration of an image-formation optical system of Example 3.
Figure 7D:
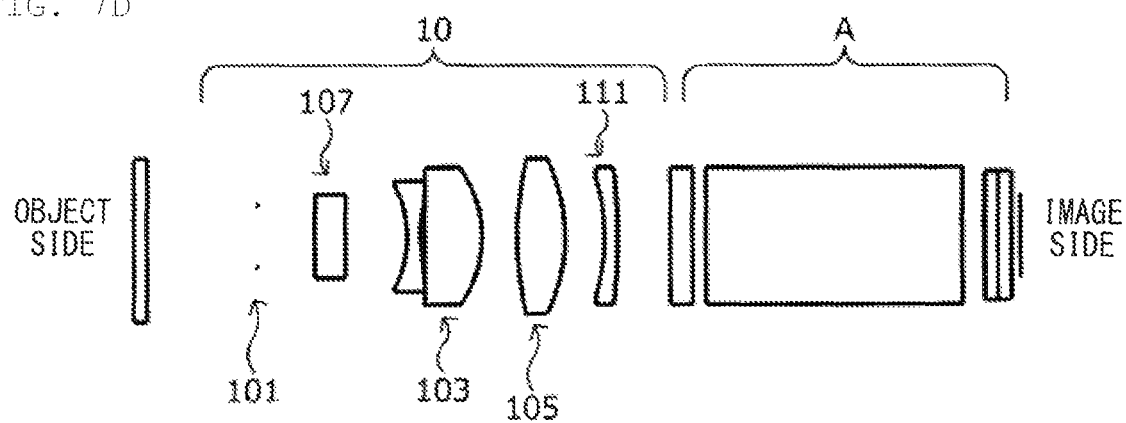
FIG. 7D is a schematic view of a configuration of an image-formation optical system of Example 4.
Figure 7E:
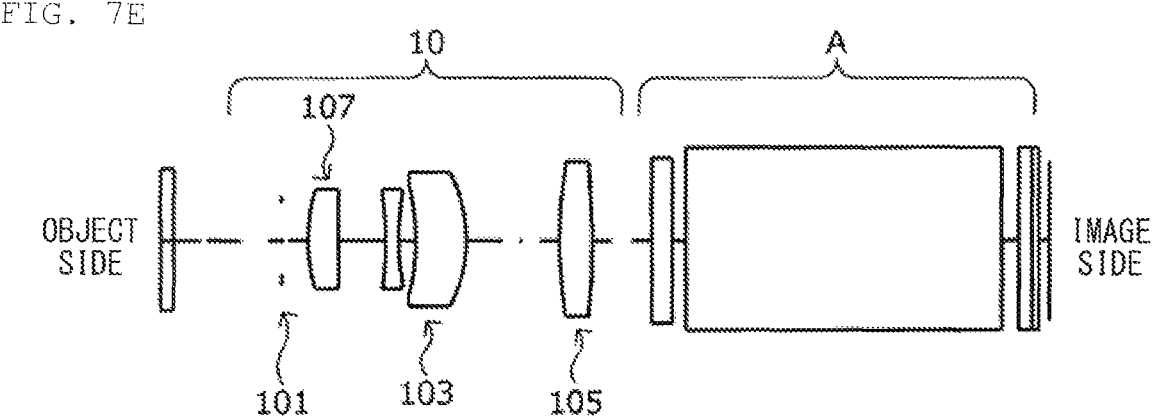
FIG. 7E is a schematic view of a configuration of an image-formation optical system of Example 5.

In the following Examples, the image-formation optical system 10 of Example 1 illustrated in FIG. 7A, the image-formation optical system 10 of Example 2 illustrated in FIG. 7B, the image-formation optical system 10 of Example 3 illustrated in FIG. 7C, the image-formation optical system 10 of Example 4 illustrated in FIG. 7D, and the image-formation optical system 10 of Example 5 illustrated in FIG. 7E are each used, and a commercially available lens design application (Code V manufactured by Synopsys, Inc.) is used, to perform a simulation on optical characteristics of each image-formation optical system 10.

Here, in each of the following FIGS. 7A to 7E, a portion represented by a reference sign A corresponds to a portion in which a lens configuration corresponding to the color-separation prism 201 (e.g., the color-separation prism 201 illustrated in FIG. 3) according to the present disclosure is set, owing to necessity of condition setting for performing the simulation.

Further, Examples 1 to 3 illustrated in FIGS. 7A to 7C are each an example of the image-formation optical system 10 including the first to fourth lens groups, Example 4 illustrated in FIG. 7D is an example of the image-formation optical system 10 including the first to third lens groups and the fifth lens group, and Example 5 illustrated in FIG. 7E is an example of the image-formation optical system 10 including the first to third lens groups.

Hereinafter, a setting condition for each Example and obtained simulation results will be described in detail.

Example 1

The image-formation optical system 10 of Example 1 illustrated in FIG. 7A is an image-formation optical system achieved by the first lens group including three lenses, and the second to fourth lens groups each including one lens.

Here, lens parameters of the respective lenses are as indicated in Table 1 below.

TABLE 1

Table 1

| Example 1 | | R | D | index | Abe |
|---|---|---|---|---|---|
| 1 | 1 | ∞ | 0.700 | 1.76820 | 71.7991 |
| 1 | 2 | ∞ | 0.000 | | |
| Diaphragm | 3 | | | | |
| 2 | 4 | 11.730 | 1.535 | 1.91048 | 31.3145 |
| 2 | 5 | −68.406 | 2.109 | | |
| 3 | 6 | −17.344 | 0.700 | 1.73432 | 28.3200 |
| 3 | 7 | 8.460 | 2.132 | | |
| 4 | 8 | −7.258 | 2.261 | 1.70444 | 30.0500 |
| 5 | 9 | 20.948 | 2.800 | 1.73234 | 54.6727 |
| 5 | 10 | −11.199 | 0.000 | | |
| 6 | 11 | −55.764 | 1.672 | 1.73234 | 54.6727 |
| 6 | 12 | −17.236 | 2.353 | | |
| 7 | 13 | 21.247 | 2.113 | 1.69980 | 55.4589 |
| 7 | 14 | −47.976 | 3.750 | | |
| 8 | 15 | ∞ | 1.090 | 1.51500 | 85.6667 |
| 8 | 16 | ∞ | 0.700 | | |
| 9 | 17 | ∞ | 12.000 | 1.60718 | 38.0267 |
| 9 | 18 | ∞ | 0.930 | | |
| 10 | 19 | ∞ | 0.700 | 1.51872 | 64.1664 |
| 11 | 20 | ∞ | 0.500 | 1.51872 | 64.1664 |
| 11 | 21 | ∞ | 0.400 | | |
| IMG | 22 | ∞ | | | |

Further, values of the respective parameters of the expressions (101) to (106), which are achieved by such lens groups, are as indicated in Table 2 below.

TABLE 2

Table 2

| | | Example 1 |
|---|---|---|
| Entrance pupil diameter [mm] | | 4 |
| Focal length f | Furthest | 16.60 |
| [mm] | 1 m | 16.49 |
| | Closest | 16.32 |
| F-number | | 4.1 |
| Maximum image height | | 2.9 |
| L [mm] | | 26.28 |
| Fb [mm] | Furthest | 14.19 |
| | 1 m | 14.76 |
| | Closest | 15.61 |
| f2 [mm] | | 21.31 |
| f4 [mm] | | −8.37 |
| R3 | | 11.73 |
| Fb/f | Furthest | 0.85 |
| (Expression 101) | 1 m | 0.90 |
| | Closest | 0.96 |

TABLE 2-continued

Table 2

| | Example 1 |
|---|---|
| L/f (Expression 102) | 1.59 |
| f2/f (Expression 103) | 1.29 |
| f4/f (Expression 104) | −0.51 |
| R3/f (Expression 105) | 0.71 |
| Amount of misalignment (Expression 106) | 0.0049 |

Figure 8B:
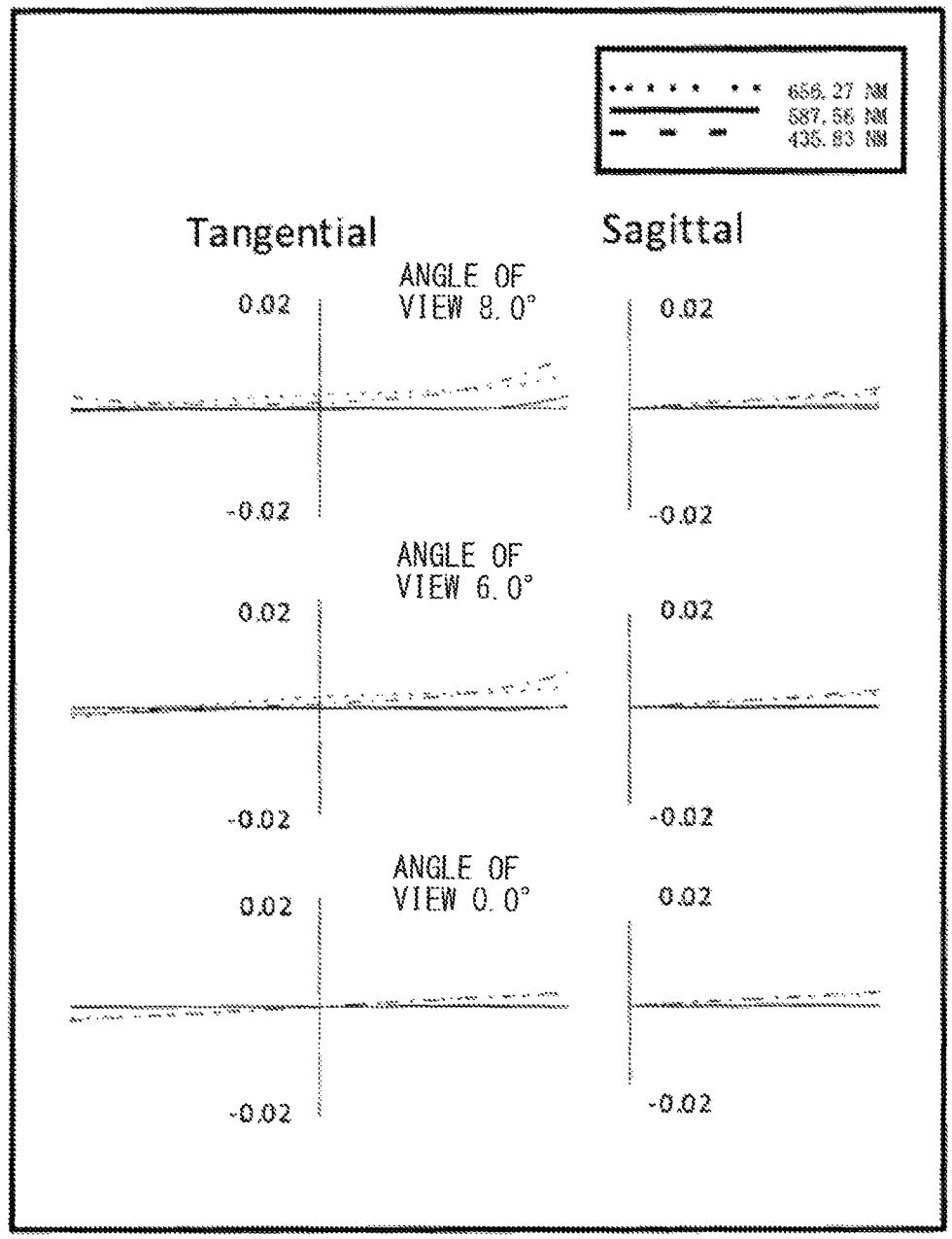
FIG. 8B is a graph indicating a simulation result of lateral aberration of the image-formation optical system of Example 1.
Figure 8C:
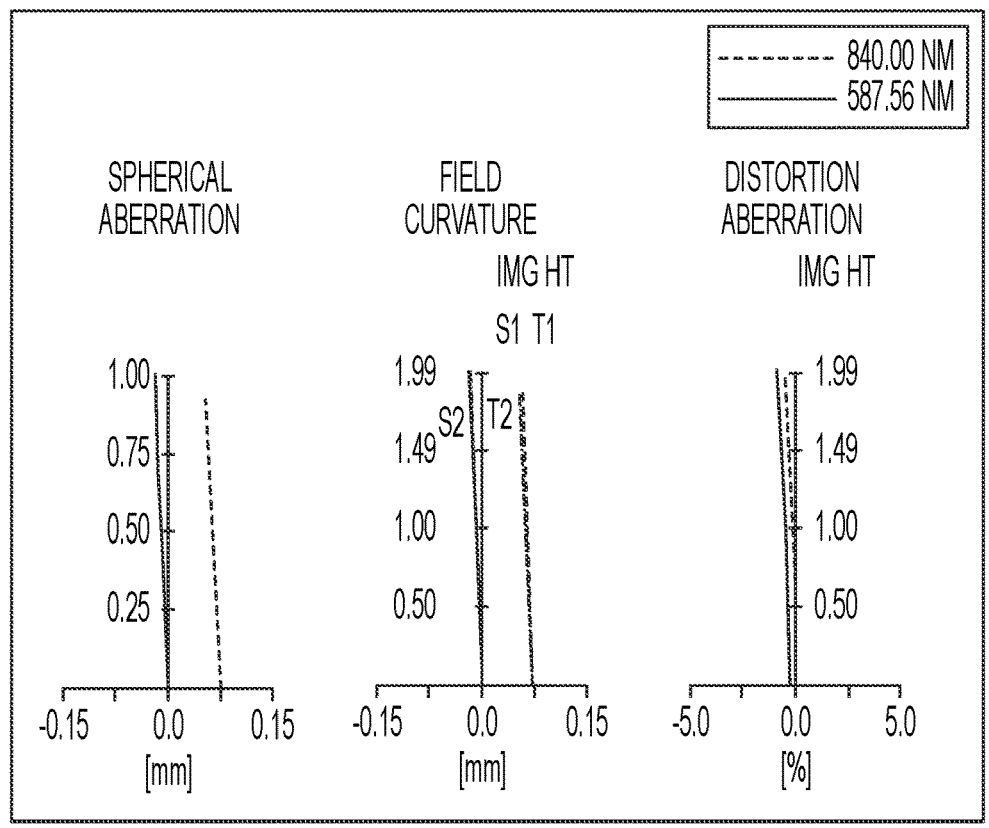
FIG. 8C is a graph indicating a simulation result of longitudinal aberration of the image-formation optical system of Example 1.

Further, obtained aberration diagrams are illustrated in FIGS. 8A to 8C. FIG. 8A is a longitudinal aberration diagram in the visible light wavelength band of the image-formation optical system 10 of Example 1, FIG. 8B is a lateral aberration diagram in the visible light wavelength band of the image-formation optical system 10 of Example 1, and FIG. 8C is a longitudinal aberration diagram illustrating longitudinal aberration in the visible light wavelength band and longitudinal aberration in the fluorescence wavelength band together. Further, FIGS. 8A and 8C each illustrate spherical aberration, field curvature, and distortion aberration in this order from left side.

As is clear from the aberration diagrams illustrated in FIGS. 8A to 8C, the conditional expressions (101) to (106) according to the present embodiment are each satisfied, and thus, it is appreciated that the image-formation optical system 10 of Example 1 exhibits excellent characteristics for the spherical aberration, the field curvature, the distortion aberration (FIGS. 8A and 8C) and also exhibits excellent characteristics for coma aberration (FIG. 8B).

Example 2

The image-formation optical system 10 of Example 2 illustrated in FIG. 7B is an image-formation optical system achieved by the first lens group including two lenses, and the second to fourth lens groups each including one lens.

Here, lens parameters of the respective lenses are as indicated in Table 3 below.

TABLE 3

Table 3

| Example 2 | | R | D | index | Abe |
|---|---|---|---|---|---|
| 1 | 1 | ∞ | 0.700 | 1.76820 | 71.7991 |
| 1 | 2 | ∞ | 0.000 | | |
| Diaphragm | 3 | | 0.780 | | |
| 2 | 4 | 12.383 | 1.651 | 1.91048 | 31.3145 |
| 2 | 5 | −25.539 | 1.000 | | |
| 3 | 6 | −12.209 | 0.700 | 1.60718 | 38.0100 |
| 3 | 7 | 8.899 | 1.798 | | |
| 4 | 8 | −9.308 | 2.600 | 1.85505 | 23.7844 |
| 5 | 9 | 24.399 | 2.600 | 1.77621 | 49.6235 |
| 5 | 10 | −9.542 | 2.354 | | |
| 6 | 11 | 22.092 | 1.789 | 1.77621 | 49.6235 |
| 6 | 12 | −49.937 | 3.735 | | |
| 7 | 13 | ∞ | 1.090 | 1.51500 | 85.6667 |
| 7 | 14 | ∞ | 0.700 | | |
| 8 | 15 | ∞ | 12.000 | 1.60718 | 38.0267 |
| 8 | 16 | ∞ | 0.930 | | |
| 9 | 17 | ∞ | 0.700 | 1.51872 | 64.1664 |
| 10 | 18 | ∞ | 0.500 | 1.51872 | 64.1664 |
| 10 | 19 | ∞ | 0.400 | | |
| IMG | 20 | | | | |

Further, values of the respective parameters of the expressions (101) to (106), which are achieved by such lens groups, are as indicated in Table 4 below.

TABLE 4

Table 4

| | | Example 2 |
|---|---|---|
| Entrance pupil diameter [mm] | | 4 |
| Focal length f | Furthest | 16.62 |
| [mm] | 1 m | 16.49 |
| | Closest | 16.31 |
| F-number | | 4.1 |
| Maximum image height | | 2.9 |
| L [mm] | | 26.28 |
| Fb [mm] | Furthest | 14.19 |
| | 1 m | 14.78 |
| | Closest | 15.63 |
| f2 [mm] | | 19.95 |
| f4 [mm] | | −7.66 |
| R3 | | 12.38 |
| Fb/f | Furthest | 0.85 |
| (Expression 101) | 1 m | 0.90 |
| | Closest | 0.96 |
| L/f (Expression 102) | | 1.59 |
| f2/f (Expression 103) | | 1.21 |
| f4/f (Expression 104) | | −0.46 |
| R3/f (Expression 105) | | 0.75 |
| Amount of misalignment (Expression 106) | | 0.0050 |

Figure 9A:
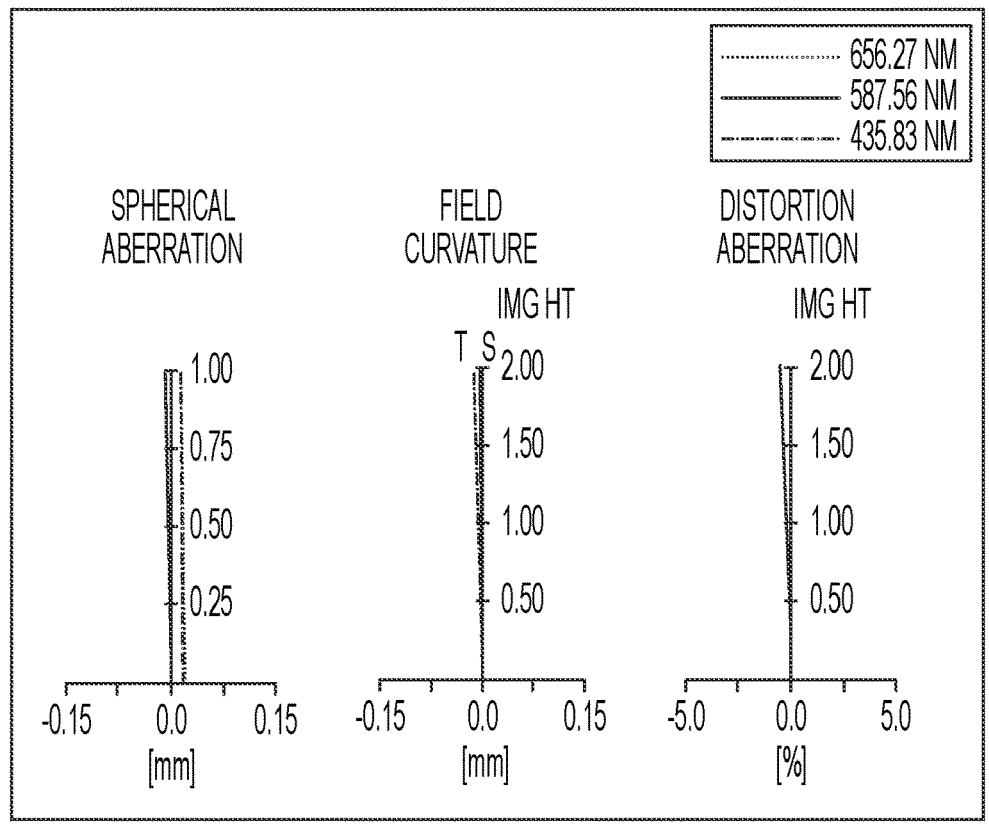
FIG. 9A is a graph indicating a simulation result of longitudinal aberration of the image-formation optical system of Example 2.
Figure 9C:
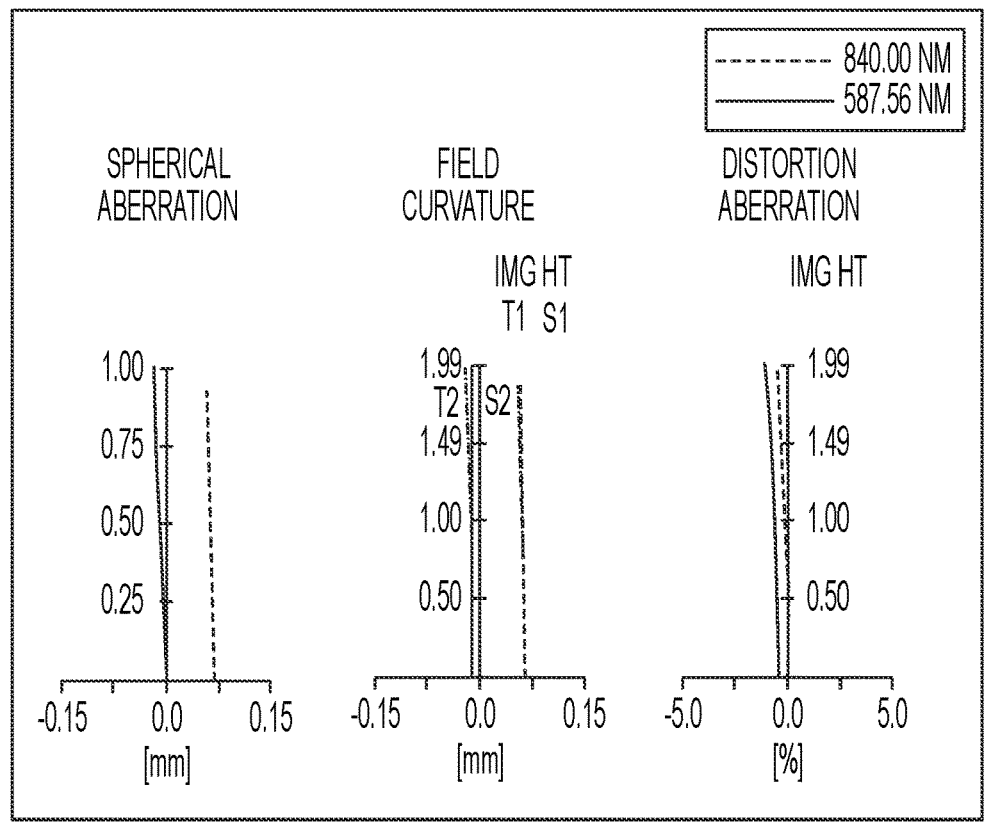
FIG. 9C is a graph indicating a simulation result of longitudinal aberration of the image-formation optical system of Example 2.

Further, obtained aberration diagrams are illustrated in FIGS. 9A to 9C. FIG. 9A is a longitudinal aberration diagram in the visible light wavelength band of the image-formation optical system 10 of Example 2, FIG. 9B is a lateral aberration diagram in the visible light wavelength band of the image-formation optical system 10 of Example 2, and FIG. 9C is a longitudinal aberration diagram illustrating longitudinal aberration in the visible light wavelength band and longitudinal aberration in the fluorescence wavelength band together. Further, FIGS. 9A and 9C each illustrate spherical aberration, field curvature, and distortion aberration in this order from left side.

As is clear from the aberration diagrams illustrated in FIGS. 9A to 9C, the conditional expressions (101) to (106) according to the present embodiment are each satisfied, and thus, it is appreciated that the image-formation optical system 10 of Example 2 exhibits excellent characteristics for the spherical aberration, the field curvature, the distortion aberration (FIGS. 9A and 9C) and also exhibits excellent characteristics for coma aberration (FIG. 9B). However, it can be appreciated that the coma aberration and the field curvature are poor as compared to the results of Example 1 illustrated in FIGS. 8A to 8C, because the number of lenses included in the first lens group 103 is smaller by one.

Example 3

The image-formation optical system 10 of Example 3 illustrated in FIG. 7C is an image-formation optical system achieved by the first lens group including three lenses, the second lens group and the third lens group each including one lens, and the fourth lens group including two lenses.

Here, lens parameters of the respective lenses are as indicated in Table 5 below.

TABLE 5

Table 5

| Example 3 | | R | D | index | Abe |
|---|---|---|---|---|---|
| 1 | 1 | ∞ | 0.700 | 1.76820 | 71.7991 |
| 1 | 2 | ∞ | 0.000 | | |
| Diaphragm | 3 | | 0.780 | | |

TABLE 5-continued

Table 5

| Example 3 | | R | D | index | Abe |
|---|---|---|---|---|---|
| 2 | 4 | | 1.500 | 1.59489 | 68.6233 |
| 2 | 5 | 23.760 | 0.100 | | |
| 3 | 6 | 32.468 | 1.876 | 1.90614 | 37.3693 |
| 4 | 7 | 10.084 | 0.620 | 1.56252 | 42.6757 |
| 4 | 8 | −110.383 | 5.502 | | |
| 5 | 9 | 6.721 | 1.260 | 1.67066 | 29.6974 |
| 5 | 10 | −6.366 | 0.669 | | |
| 6 | 11 | 61.706 | 1.332 | 1.73234 | 54.6727 |
| 6 | 12 | −12.501 | 0.100 | | |
| 7 | 13 | −9.688 | 3.024 | 1.49845 | 81.6072 |
| 7 | 14 | 24.026 | 2.742 | | |
| 8 | 15 | −46.896 | 1.955 | 1.62032 | 63.3949 |
| 8 | 16 | ∞ | 3.923 | | |
| 9 | 17 | ∞ | 1.090 | 1.51872 | 64.1664 |
| 9 | 18 | ∞ | 0.700 | | |
| 10 | 19 | ∞ | 14.765 | 1.60718 | 38.0267 |
| 10 | 20 | ∞ | 0.930 | | |
| 11 | 21 | ∞ | 0.700 | 1.51872 | 64.1664 |
| 12 | 22 | ∞ | 0.500 | 1.51872 | 64.1664 |
| 13 | 23 | ∞ | 0.400 | | |
| IMG | 24 | | | | |

Further, values of the respective parameters of the expressions (101) to (106), which are achieved by such lens groups, are as indicated in Table 6 below. It is to be noted that in this Example, it is not possible to define the focal length f4, and the conditions represented by the expression (104) is not satisfied.

TABLE 6

Table 6

| | | Example 3 |
|---|---|---|
| Entrance pupil diameter [mm] | | 6 |
| Focal length f | Furthest | 19.88 |
| [mm] | 1 m | 19.63 |
| | Closest | 19.30 |
| F-number | | 3.3 |
| Maximum image height | | 3.6 |
| L [mm] | | 33.96 |
| Fb [mm] | Furthest | 15.32 |
| | 1 m | 16.21 |
| | Closest | 17.45 |
| f2 [mm] | | 25.88 |
| f4 [mm] | | — |
| R3 | | 23.76 |
| Fb/f | Furthest | 0.77 |
| (Expression 101) | 1 m | 0.83 |
| | Closest | 0.90 |
| L/f (Expression 102) | | 1.73 |
| f2/f (Expression 103) | | 1.32 |
| f4/f (Expression 104) | | — |
| R3/f (Expression 105) | | 1.21 |
| Amount of misalignment (Expression 106) | | 0.0037 |

Figure 10A:
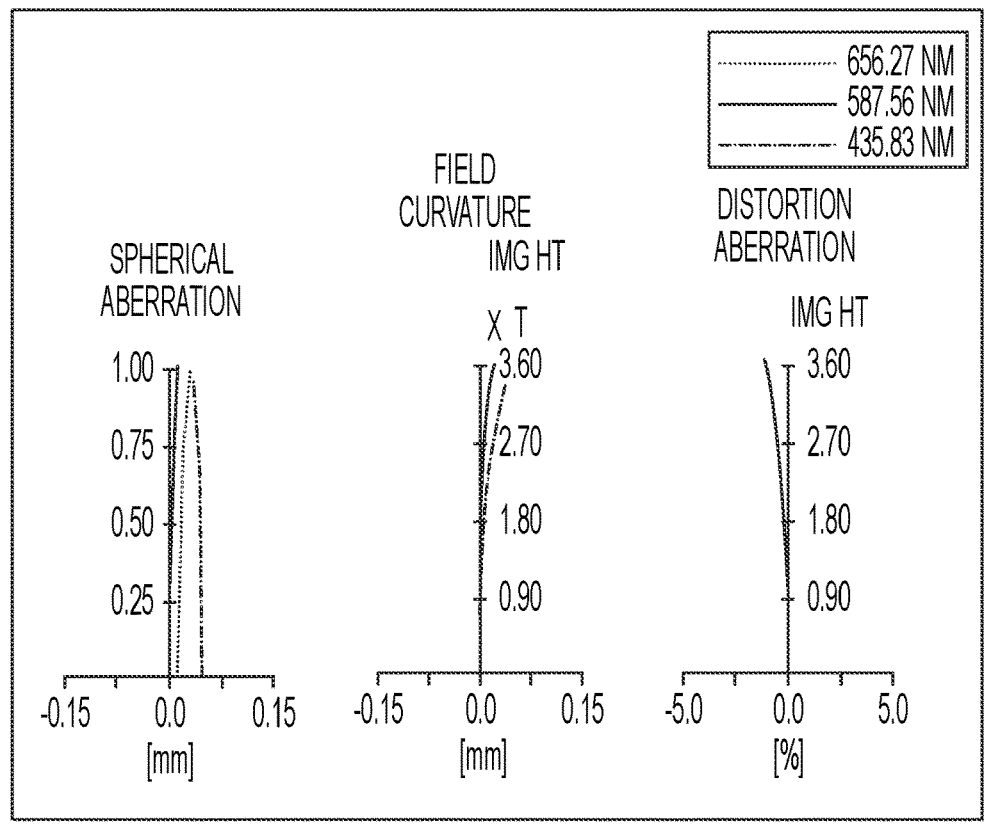
FIG. 10A is a graph indicating a simulation result of longitudinal aberration of the image-formation optical system of Example 3.
Figure 10B:
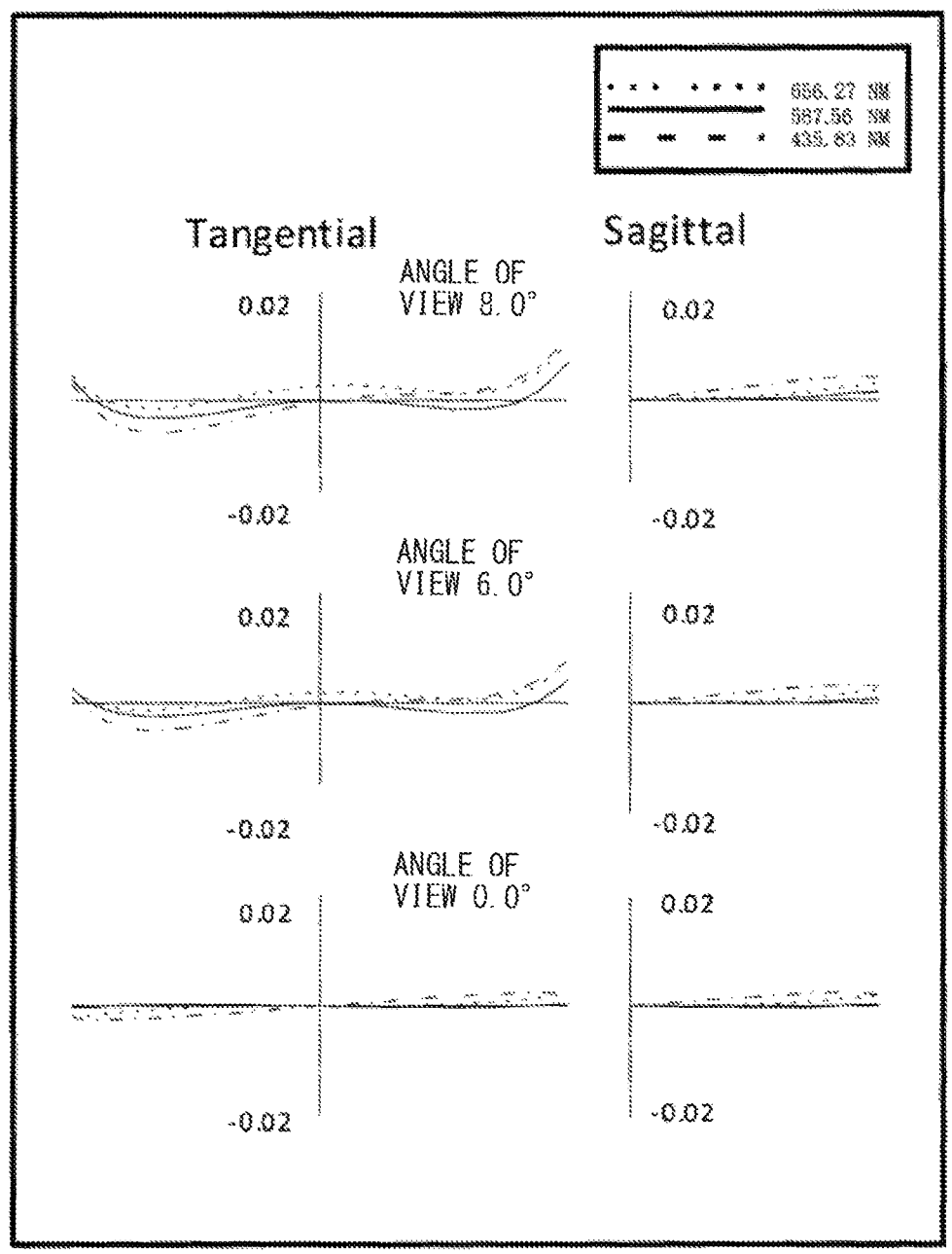
FIG. 10B is a graph indicating a simulation result of lateral aberration of the image-formation optical system of Example 3.
Figure 10C:
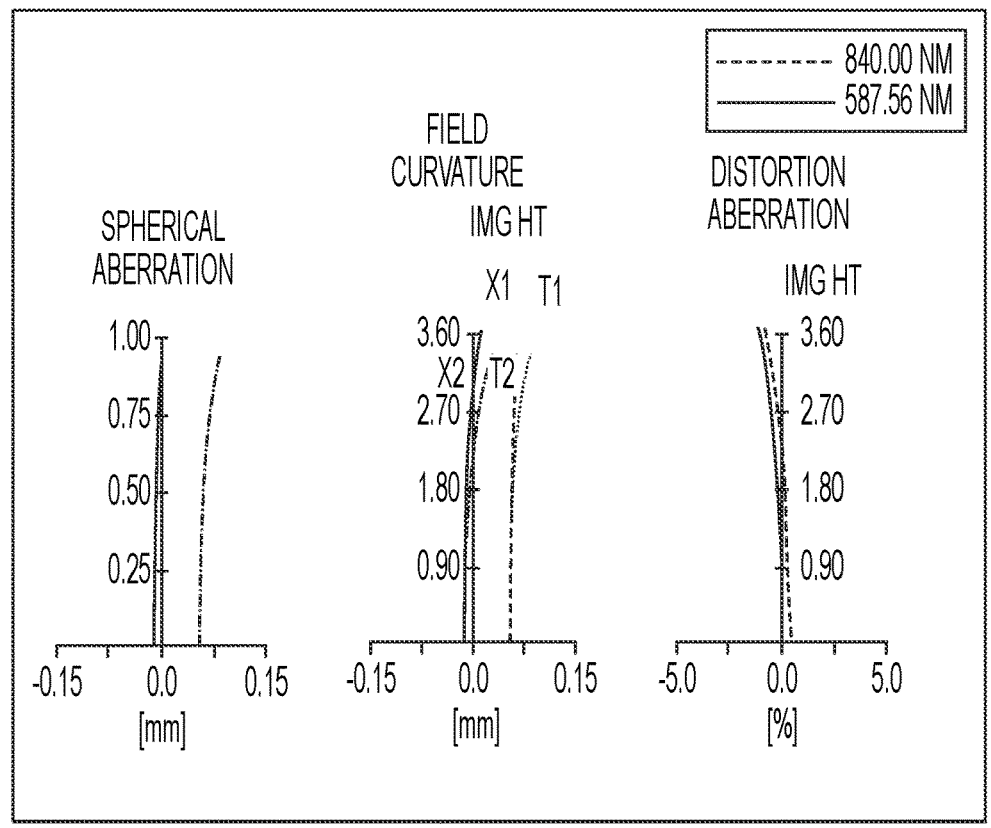
FIG. 10C is a graph indicating a simulation result of longitudinal aberration of the image-formation optical system of Example 3.

Obtained aberration diagrams are illustrated in FIGS. 10A to 10C. FIG. 10A is a longitudinal aberration diagram in the visible light wavelength band of the image-formation optical system 10 of Example 3, FIG. 10B is a lateral aberration diagram in the visible light wavelength band of the image-formation optical system 10 of Example 3, and FIG. 10C is a longitudinal aberration diagram illustrating longitudinal aberration in the visible light wavelength band and longitudinal aberration in the fluorescence wavelength band together. Further, FIGS. 10A and 10C each illustrate spherical aberration, field curvature, and distortion aberration in this order from left side.

As is clear from the aberration diagrams illustrated in FIGS. 10A to 10C, the conditional expressions (101) to (106) according to the present embodiment are each satisfied, and thus, it is appreciated that the image-formation optical system 10 of Example 3 exhibits excellent characteristics for the spherical aberration, the field curvature, the distortion aberration (FIGS. 10A and 10C) and also exhibits excellent characteristics for coma aberration (FIG. 10B).

It is to be noted that Example 3 is an example in which the entrance pupil diameter is increased and the F-number is decreased. The reduction in F-number makes it possible to increase the resolution limit, and this is an effective example in a case where high resolution is demanded in the future.

Example 4

The image-formation optical system 10 of Example 4 illustrated in FIG. 7D is an image-formation optical system achieved by the first lens group including two lenses, the second lens group and the third lens group each including one lens, and the fifth lens group including one lens.

Here, lens parameters of the respective lenses are as indicated in Table 7 below.

TABLE 7

Table 7

| Example 4 | | R | D | index | Abe |
|---|---|---|---|---|---|
| 1 | 1 | ∞ | 0.700 | 1.76820 | 71.7991 |
| 1 | 2 | ∞ | 0.000 | | |
| Diaphragm | 3 | | 0.780 | | |
| 2 | 4 | 35.969 | 1.543 | 1.88814 | 40.7993 |
| 2 | 5 | −27.606 | 2.843 | | |
| 3 | 6 | −5.049 | 0.700 | 1.78415 | 40.8809 |
| 3 | 7 | 22.028 | 0.214 | | |
| 4 | 8 | −17.878 | 2.579 | 1.59488 | 68.6290 |
| 4 | 9 | −5.285 | 1.338 | | |
| 5 | 10 | 14.584 | 2.324 | 1.59488 | 68.6290 |
| 5 | 11 | −9.124 | 2.166 | | |
| 6 | 12 | −9.284 | 0.600 | 1.62409 | 36.2994 |
| 6 | 13 | ∞ | 2.500 | | |
| 7 | 14 | ∞ | 1.090 | 1.51872 | 64.1664 |
| 7 | 15 | ∞ | 0.700 | | |
| 8 | 16 | ∞ | 12.000 | 1.60718 | 38.0267 |
| 8 | 17 | ∞ | 0.930 | | |
| 9 | 18 | ∞ | 0.700 | 1.51872 | 64.1664 |
| 10 | 19 | ∞ | 0.500 | 1.51872 | 64.1664 |
| 10 | 20 | ∞ | 0.400 | | |
| IMG | 21 | | | | |

Further, values of the respective parameters of the expressions (101) to (106), which are achieved by such lens groups, are as indicated in Table 8 below. It is to be noted that in this Example, the focal length f4 is defined as in Table 10 below, and as a result, the condition represented by the expression (104) is not satisfied.

TABLE 8

Table 8

| | | Example 4 |
|---|---|---|
| Entrance pupil diameter [mm] | | 2.5 |
| Focal length f | Furthest | 17.05 |
| [mm] | 1 m | 16.61 |
| | Closest | 15.78 |
| F-number | | 6.6 |
| Maximum image height | | 2.4 |
| L [mm] | | 27.29 |
| Fb [mm] | Furthest | 13.52 |
| | 1 m | 13.52 |
| | Closest | 13.52 |
| f2 [mm] | | 9.79 |

TABLE 8-continued

Table 8

| | | Example 4 |
|---|---|---|
| f4 [mm] | | −5.18 |
| R3 | | 35.97 |
| Fb/f | Furthest | 0.79 |
| (Expression 101) | 1 m | 0.81 |
| | Closest | 0.86 |
| L/f (Expression 102) | | 1.64 |
| f2/f (Expression 103) | | 0.59 |
| f4/f (Expression 104) | | −0.31 |
| R3/f (Expression 105) | | 2.17 |
| Amount of misalignment (Expression 106) | | 0.0047 |

Figure 11A:
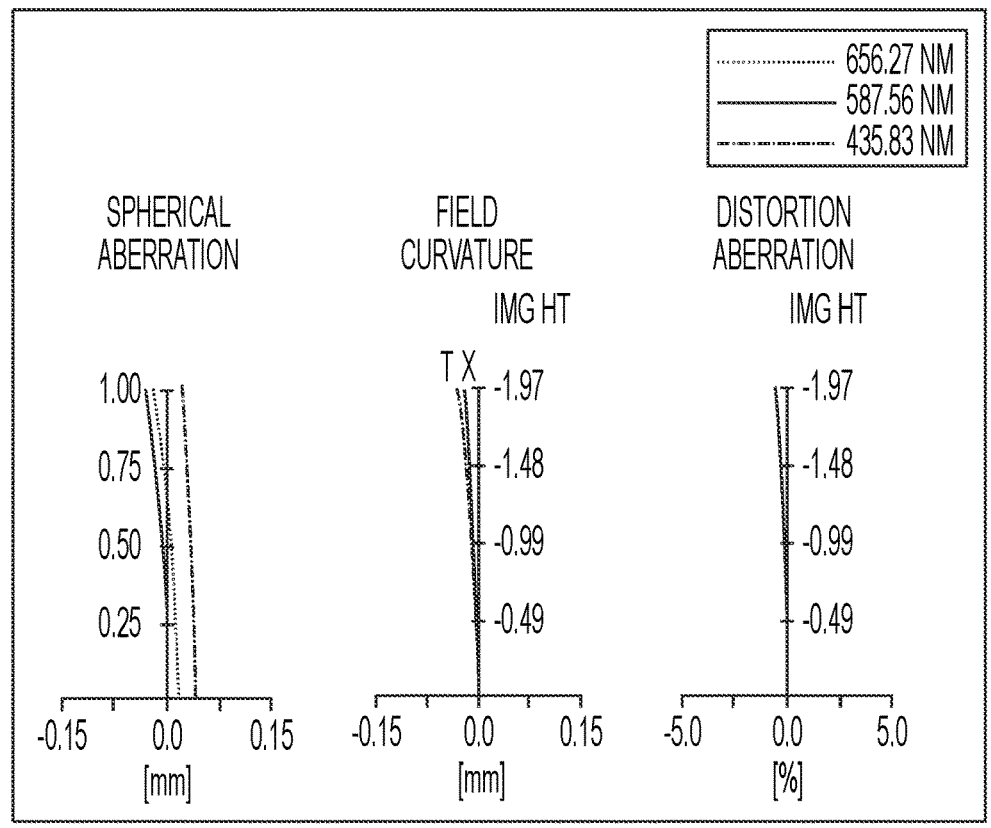
FIG. 11A is a graph indicating a simulation result of longitudinal aberration of the image-formation optical system of Example 4.
Figure 11C:
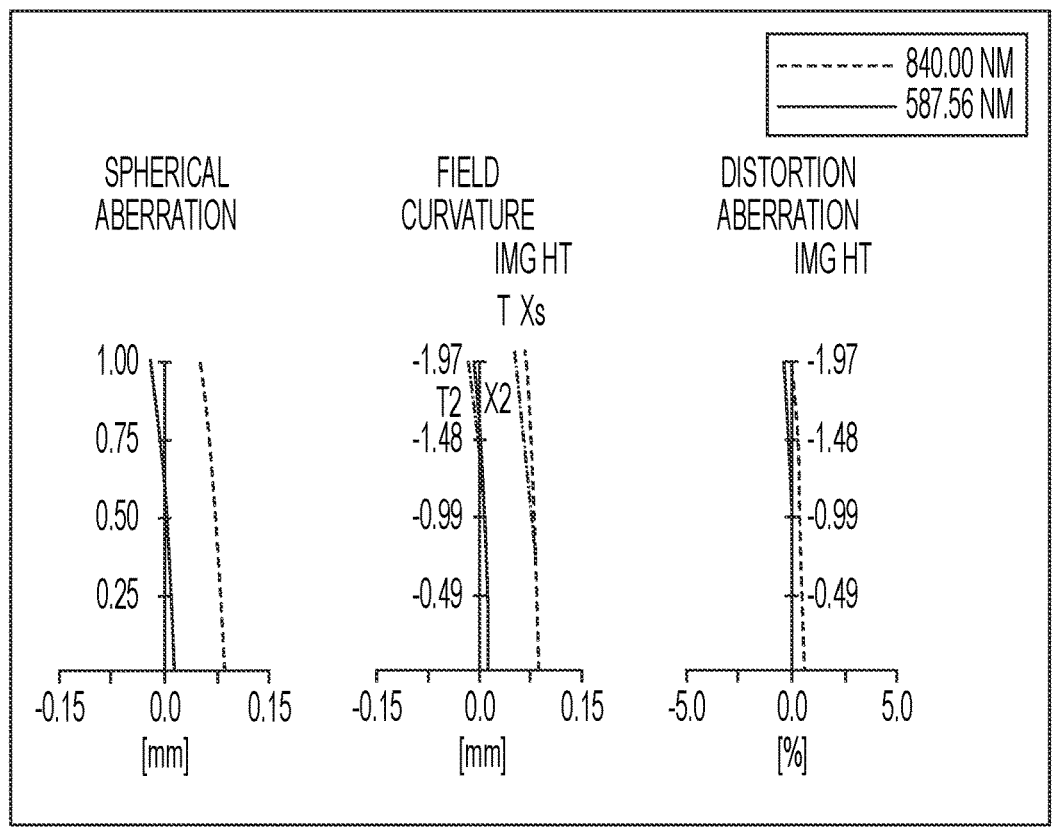
FIG. 11C is a graph indicating a simulation result of longitudinal aberration of the image-formation optical system of Example 4.

Obtained aberration diagrams are illustrated in FIGS. 11A to 11C. FIG. 11A is a longitudinal aberration diagram in the visible light wavelength band of the image-formation optical system 10 of Example 4, FIG. 11B is a lateral aberration diagram in the visible light wavelength band of the image-formation optical system 10 of Example 4, and FIG. 11C is a longitudinal aberration diagram illustrating longitudinal aberration in the visible light wavelength band and longitudinal aberration in the fluorescence wavelength band together. Further, FIGS. 11A and 11C each illustrate spherical aberration, field curvature, and distortion aberration in this order from left side.

As is clear from the aberration diagrams illustrated in FIGS. 11A to 11C, the conditional expressions (101) to (103) and the conditional expressions (105) to (106) according to the present embodiment are each satisfied, and thus, it is appreciated that the image-formation optical system 10 of Example 4 exhibits excellent characteristics for the spherical aberration, the field curvature, the distortion aberration (FIGS. 11A and 11C) and also exhibits excellent characteristics for coma aberration (FIG. 11B).

It is to be noted that Example 4 is an example in which the entrance pupil diameter is decreased and compatibility is limited only to a rigid scope having a relatively small diameter. The limitation in the compatible rigid scope lowers degree of design difficulty, and makes aberration correction easier while reducing the number of lenses.

Example 5

The image-formation optical system 10 of Example 5 illustrated in FIG. 7E is an image-formation optical system achieved by the first lens group including two lenses, and the second lens group and the third lens group each including one lens.

Here, lens parameters of the respective lenses are as indicated in Table 9 below.

TABLE 9

Table 9

| Example 5 | | R | D | index | Abe |
|---|---|---|---|---|---|
| 1 | 1 | ∞ | 0.700 | 1.76820 | 71.7991 |
| 1 | 2 | ∞ | 0.000 | | |
| Diaphragm | 3 | | 0.780 | | |
| 2 | 4 | 13.952 | 1.545 | 1.96073 | 32.3194 |
| 2 | 5 | −113.878 | 2.722 | | |
| 3 | 6 | −13.480 | 0.700 | 1.83348 | 23.5319 |
| 3 | 7 | 13.545 | 1.036 | | |
| 4 | 8 | −9.166 | 2.800 | 1.62286 | 60.3227 |
| 4 | 9 | −7.198 | 2.000 | | |
| 5 | 10 | 19.581 | 1.789 | 1.62033 | 63.3990 |

TABLE 9-continued

Table 9

| Example 5 | | R | D | index | Abe |
|---|---|---|---|---|---|
| 5 | 11 | −84.372 | 4.772 | | |
| 6 | 12 | ∞ | 1.090 | 1.51872 | 64.1664 |
| 6 | 13 | ∞ | 0.700 | | |
| 7 | 14 | ∞ | 17.624 | 1.60718 | 38.0267 |
| 7 | 15 | ∞ | 0.930 | | |
| 8 | 16 | ∞ | 0.700 | 1.51872 | 64.1664 |
| 9 | 17 | ∞ | 0.500 | 1.51872 | 64.1664 |
| 9 | 18 | ∞ | 0.400 | | |
| IMG | 19 | | | | |

Further, values of the respective parameters of the expressions (101) to (106), which are achieved by such lens groups, are as indicated in Table 10 below. It is to be noted that in this Example, the air-equivalent optical path length L from the image-formation optical system 10 to the color-separation-prism optical system is defined as in Table 12, and as a result, the condition represented by the expression (102) is not satisfied. In addition, in this Example, the focal length f4 is defined as in Table 12 below, and as a result, the condition represented by the expression (104) is not satisfied.

TABLE 10

Table 10

| | | Example 5 |
|---|---|---|
| Entrance pupil diameter [mm] | | 4 |
| Focal length f | Furthest | 24.56 |
| [mm] | 1 m | 24.27 |
| | Closest | 23.85 |
| F-number | | 6.1 |
| Maximum image height | | 4.3 |
| L [mm] | | 32.15 |
| Fb [mm] | Furthest | 18.03 |
| | 1 m | 19.29 |
| | Closest | 21.21 |
| f2 [mm] | | 25.79 |
| f4 [mm] | | −8.01 |
| R3 | | 13.95 |
| Fb/f | Furthest | 0.73 |
| (Expression 101) | 1 m | 0.79 |
| | Closest | 0.89 |
| L/f (Expression 102) | | 1.32 |
| f2/f (Expression 103) | | 1.06 |
| f4/f (Expression 104) | | −0.33 |
| R3/f (Expression 105) | | 0.57 |
| Amount of misalignment (Expression 106) | | 0.0048 |

Figure 12A:
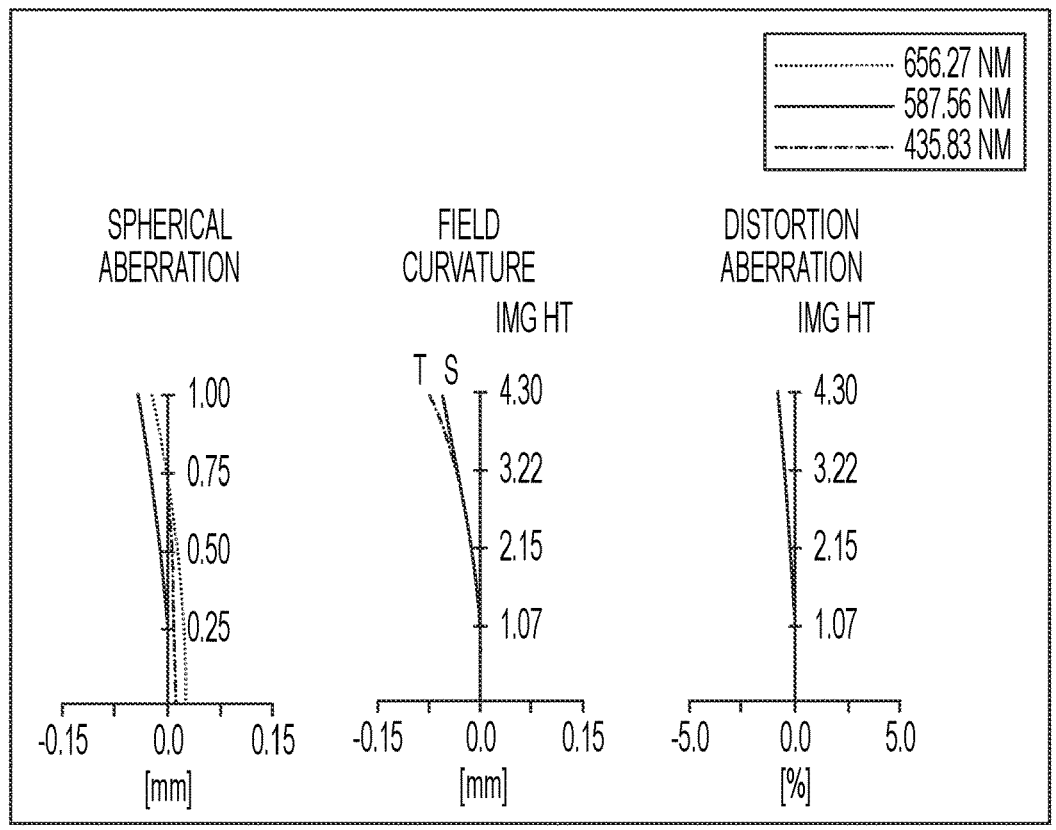
FIG. 12A is a graph indicating a simulation result of longitudinal aberration of the image-formation optical system of Example 5.
Figure 12B:
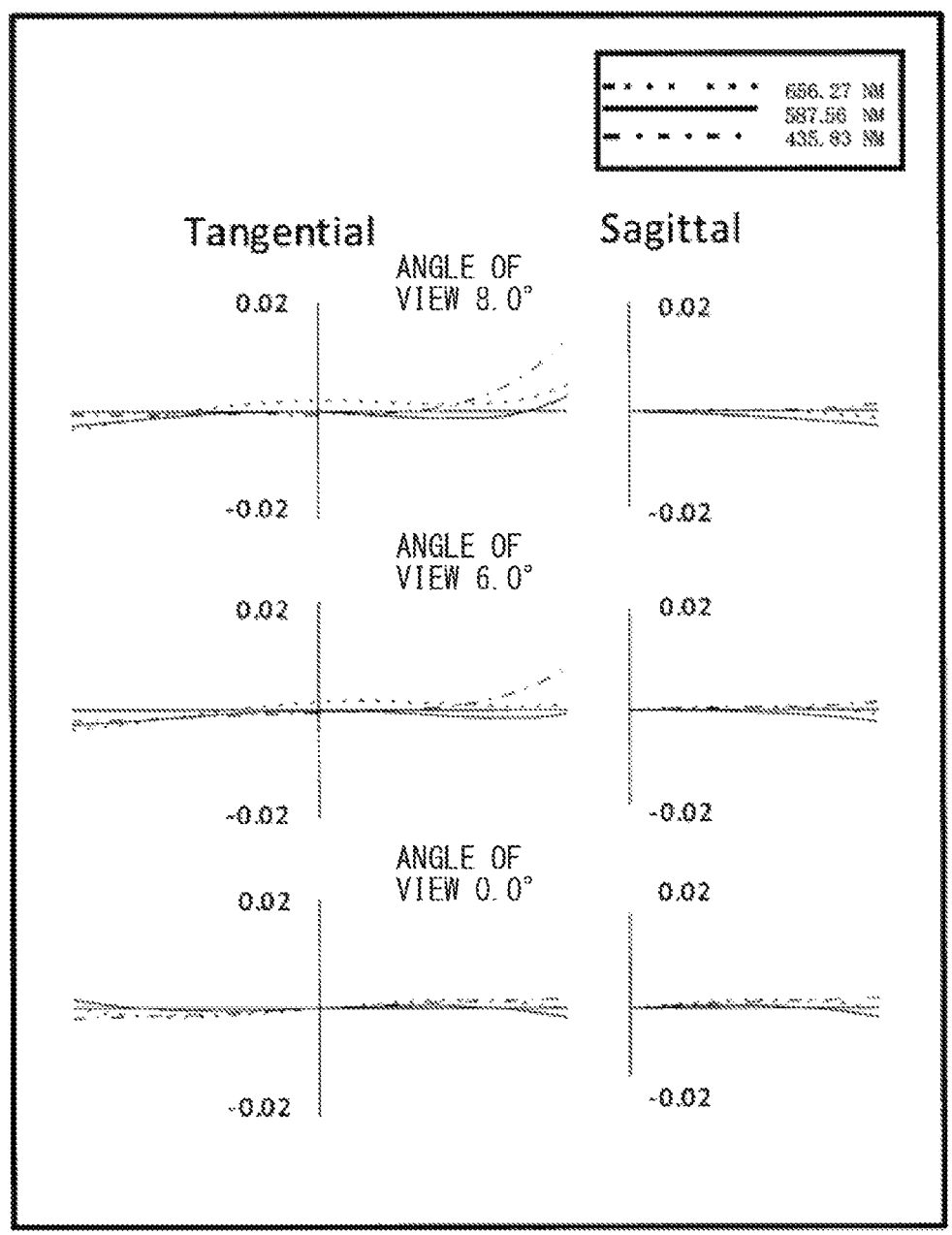
FIG. 12B is a graph indicating a simulation result of lateral aberration of the image-formation optical system of Example 5.
Figure 12C:
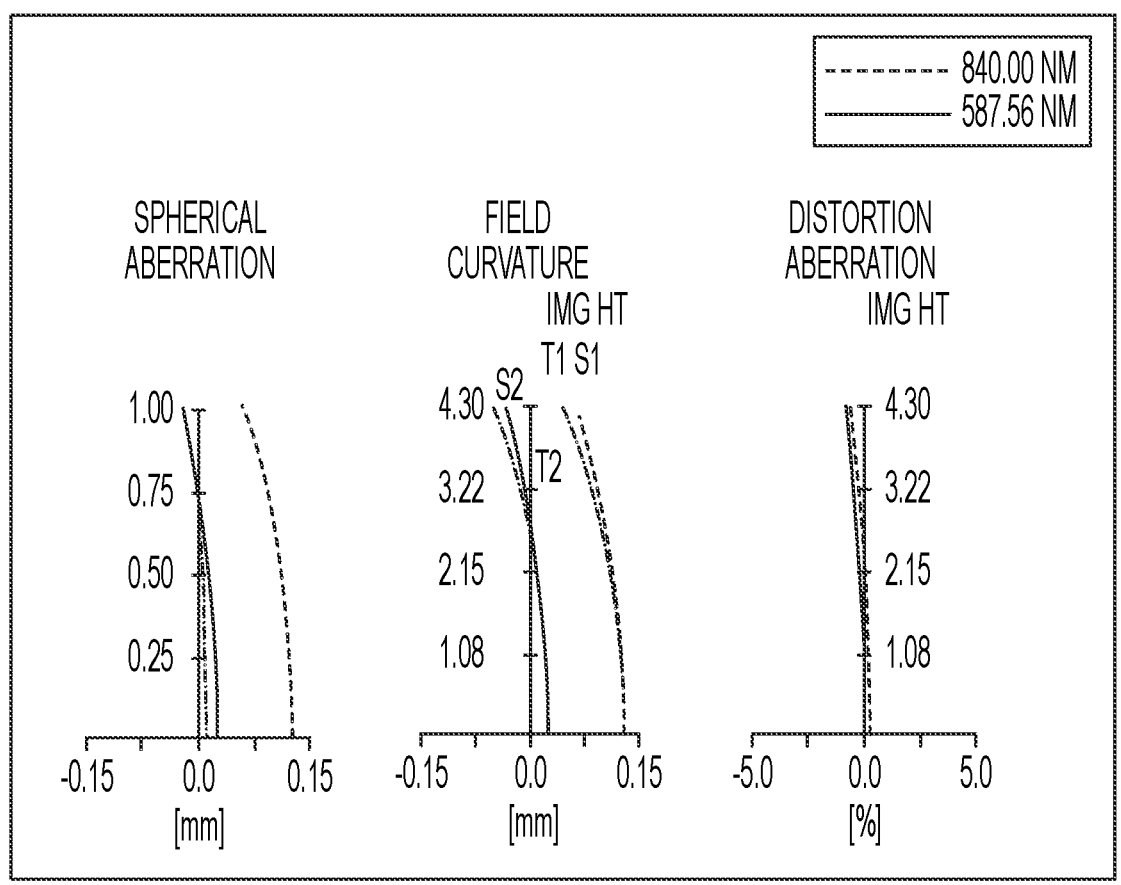
FIG. 12C is a graph indicating a simulation result of longitudinal aberration of the image-formation optical system of Example 5.

Obtained aberration diagrams are illustrated in FIGS. 12A to 12C. FIG. 12A is a longitudinal aberration diagram in the visible light wavelength band of the image-formation optical system 10 of Example 5, FIG. 12B is a lateral aberration diagram in the visible light wavelength band of the image-formation optical system 10 of Example 5, and FIG. 12C is a longitudinal aberration diagram illustrating longitudinal aberration in the visible light wavelength band and longitudinal aberration in the fluorescence wavelength band together. Further, FIGS. 12A and 12C each illustrate spherical aberration, field curvature, and distortion aberration in this order from left side.

As is clear from the aberration diagrams illustrated in FIGS. 12A to 12C, the conditional expressions (101) to (103) and the conditional expressions (105) to (106) according to the present embodiment are each satisfied, and thus, it is appreciated that the image-formation optical system 10 of Example 5 exhibits excellent characteristics for the spherical aberration, the field curvature, the distortion aberration (FIGS. 12A and 12C) and also exhibits excellent characteristics for coma aberration (FIG. 12B).

It is to be noted that such an Example is a case in which a size of the imaging device is increased. Although the entrance pupil diameter is the same as Example 1 or the like, the increase in focal length for obtaining the same angle of view makes it possible to increase the F-number. For this reason, the spherical aberration rarely occurs, and it becomes possible to achieve a design with a small number of lenses.

A preferred embodiment of the present disclosure has/have been described above in detail with reference to the accompanying drawings, but the technical scope of the present disclosure is not limited to such an embodiment. It is apparent that a person having ordinary skill in the art of the present disclosure can arrive at various alterations and modifications within the scope of the technical idea described in the appended claims, and it is understood that such alterations and modifications naturally fall within the technical scope of the present disclosure.

Furthermore, the effects described herein are merely illustrative and exemplary, and not limiting. That is, the technique according to the present disclosure can exert other effects that are apparent to those skilled in the art from the description herein, in addition to the above-described effects or in place of the above-described effects.

It is to be noted that the following configurations also belong to the technical scope of the present disclosure.

(1)
A rigid-scope optical system including:
an image-formation optical system that causes an image in each of wavelength bands to be formed in a predetermined imaging device, the wavelength bands including a fluorescence wavelength band belonging to a near-infrared light wavelength band and a visible light wavelength band; and
a color-separation-prism optical system having a dichroic film that separates an optical path of light to be imaged by the image-formation optical system into an optical path of the visible light wavelength band and an optical path of the fluorescence wavelength band, in which
the image-formation optical system causes the respective images to be formed in a fluorescence imaging device and a visible light imaging device, the fluorescence imaging device and the visible light imaging device being disposed to cause an amount of misalignment between a fluorescence image formation position and a visible light image formation position caused by the image-formation optical system to correspond to a difference between an optical path length of fluorescence and an optical path length of visible light, the fluorescence and the visible light forming the respective images via the color-separation-prism optical system, and
where a focal length of the image-formation optical system is represented by f [mm], and an air-equivalent optical path length from the image-formation optical system to an imaging device is represented by Fb [mm], the image-formation optical system has the focal length and the air-equivalent optical path length that satisfy a condition represented by the following expression (1), $Fb/f > 0.72$ \hfill expression (1).

(2)
The rigid-scope optical system according to (1), in which the image-formation optical system includes, in order from object side to image side,
at least a diaphragm, a first lens group having a positive refractive power, and a second lens group having a positive refractive power,
the first lens group including, in order from the object side to the image side, a lens having a negative refractive power with a concave surface facing the object side, and at least one lens having a positive refractive power,
the second lens group being a focus group that performs focusing depending on an object distance, and
the image-formation optical system satisfies a condition represented by the following expression (2), where an air-equivalent optical path length from the image-formation optical system to the color-separation-prism optical system is represented by L [mm], $1.4 < L/f < 1.8$ \hfill expression (2).

(3)
The rigid-scope optical system according to (2), in which the image-formation optical system further includes, between the diaphragm and the first lens group, in order from the object side to the image side, at least one of a third lens group having a positive refractive power or a fourth lens group having a negative refractive power, and
the fourth lens group satisfies a condition represented by the following expression (3), where a focal length of the fourth lens group in the image-formation optical system is represented by f4 [mm], $-0.80 < f4/f < -0.35$ \hfill expression (3)

(4)
The rigid-scope optical system according to (3), in which the image-formation optical system includes the third lens group, and
the second lens group further satisfies a relationship represented by the following expression (4), where a curvature radius at an object-side surface of a lens located on most object side in the third lens group is represented by R3 [mm], $0.85 < R3/f$ \hfill expression (4).

(5)
The rigid-scope optical system according to any one of (2) to (4), in which
the second lens group in the image-formation optical system further satisfies a condition represented by the following expression (5), where a focal length of the second lens group is represented by f2 [mm], $1.0 < f2/f < 1.4$ \hfill expression (5)

(6)
The rigid-scope optical system according to any one of (2) to (5), in which the image-formation optical system further includes a fifth lens group having a negative refractive power at a subsequent stage of the second lens group.

(7)
The rigid-scope optical system according to any one of (1) to (6), in which the image-formation optical system satisfies a condition represented by the following expression (6), where a focal length at a fluorescence wavelength of the image-formation optical system is represented by f(NIR)

[mm], and a focal length at a visible light wavelength of the image-formation optical system is represented by f(V) [mm], $$0.0025 < (f(NIR) - f(V))/f(V) < 0.0060 \quad \text{expression (6)}$$

(8)

The rigid-scope optical system according to (7), in which
the visible light imaging device is fixed at a position on an image-formation surface of the image-formation optical system, and
the fluorescence imaging device is fixed at a position in which an optical path difference satisfies the expression (6).

(9)

The rigid-scope optical system according to (7), in which
the visible light imaging device is fixed at a position on an image-formation surface of the image-formation optical system,
the fluorescence imaging device is provided to allow a separation distance from the color-separation-prism optical system to be variable, and
the rigid-scope optical system further includes a fluorescence picture image focusing mechanism that varies an optical path difference to cause the expression (6) to be satisfied.

(10)

The rigid-scope optical system according to any one of (1) to (9), in which the color-separation-prism optical system includes
a color-separating prism including the dichroic film, and
a bandpass filter provided between the color-separating prism and the fluorescence imaging device, the bandpass filter having an entrance surface perpendicular to an optical axis.

(11)

The rigid-scope optical system according to (10), in which
the dichroic film has a transmittance of 90% or more in a wavelength band of 780 to 880 nm, and a transmittance of 10% or less in a wavelength band of 400 to 720 nm, and
the bandpass filter has a transmittance of 90% or more in a wavelength band of 813 to 850 nm, and a transmittance of 10% or less in a wavelength band of 350 to 805 nm.

(12)

An imaging apparatus including a rigid-scope optical system, the rigid-scope optical system including
an image-formation optical system that causes an image in each of wavelength bands to be formed in a predetermined imaging device, the wavelength bands including a fluorescence wavelength band belonging to a near-infrared light wavelength band and a visible light wavelength band,
a color-separation-prism optical system having a dichroic film that separates an optical path of light to be imaged by the image-formation optical system into an optical path of the visible light wavelength band and an optical path of the fluorescence wavelength band,
a visible light imaging device that forms an image of the visible light wavelength band, and
a fluorescence imaging device that forms an image in the fluorescence wavelength band, in which
the visible light imaging device and the fluorescence imaging device are disposed to cause an optical path difference between an optical path length of a visible light wavelength band and an optical path length of a fluorescence wavelength band to correspond to an amount of misalignment between a fluorescence image formation position and a visible light image formation position caused by the image-formation optical system, the visible light forming an image in the visible light imaging device via the color-separation-prism optical system, the fluorescence forming an image in the fluorescence imaging device via the color-separation-prism optical system, and,
where a focal length of the image-formation optical system is represented by f [mm], and an air-equivalent optical path length from the image-formation optical system to an imaging device is represented by Fb [mm], the image-formation optical system has the focal length and the air-equivalent optical path length that satisfy a condition represented by the following expression (1), $$Fb/f > 0.72 \quad \text{expression (1).}$$

(13)

An endoscope unit including:
a rigid-scope unit that generates an image of a predetermined imaging target of a fluorescence wavelength band belonging to a near-infrared light wavelength band and an image of the predetermined imaging target of a visible light wavelength band;
an imaging unit that includes a rigid-scope optical system coupled to the rigid-scope unit, a visible light imaging device in which the image of the visible light wavelength band is formed, and a fluorescence imaging device in which the image of the fluorescence wavelength band is formed, and generates a captured picture image of the imaging target of the fluorescence wavelength band and a captured picture image of the imaging target of the visible light wavelength band, in which
the rigid-scope optical system includes
an image-formation optical system that causes an image in each of the fluorescence wavelength band and the visible light wavelength band to be formed in a predetermined imaging device, and
a color-separation-prism optical system having a dichroic film that separates an optical path of light to be imaged by the image-formation optical system into an optical path of the visible light wavelength band and an optical path of the fluorescence wavelength band,
the visible light imaging device and the fluorescence imaging device are disposed to cause an optical path difference between an optical path length of a visible light wavelength band and an optical path length of a fluorescence wavelength band to correspond to an amount of misalignment between a fluorescence image formation position and a visible light image formation position caused by the image-formation optical system, the visible light forming an image in the visible light imaging device via the color-separation-prism optical system, the fluorescence forming an image in the fluorescence imaging device via the color-separation-prism optical system, and,
where a focal length of the image-formation optical system is represented by f [mm], and an air-equivalent optical path length from the image-formation optical system to an imaging device is represented by Fb [mm], the image-formation optical system has the focal length and the air-equivalent optical path length that satisfy a condition represented by the following expression (1), $$Fb/f > 0.72 \quad \text{expression (1).}$$

REFERENCE SIGNS LIST 1 rigid-scope optical system
3 visible light imaging device
4 fluorescence imaging device
10 image-formation optical system
20 color-separation-prism optical system
30 fluorescence picture image focusing mechanism
101 diaphragm
103 first lens group
105 second lens group
107 third lens group
109 fourth lens group
111 fifth lens group
201 color-separation prism
203 dichroic film
211 first prism
213 second prism
215 narrow-band bandpass filter
217 infrared cut filter
500 endoscope system
501 rigid-scope unit
503 imaging unit
505 CCU
507 display apparatus

The invention claimed is:

1. A scope optical system comprising:
an image-formation optical system configured to form an image in each of wavelength bands to in a predetermined imaging sensor, the wavelength bands including a fluorescence wavelength band belonging to a near-infrared light wavelength band and a visible light wavelength band; and
a color-separation-prism optical system having a dichroic film constructed to separate an optical path of light to be imaged by the image-formation optical system into an optical path of the visible light wavelength band and an optical path of the fluorescence wavelength band, wherein
the image-formation optical system is configured to form the respective images in a fluorescence imaging sensor and a visible light imaging sensor, the fluorescence imaging sensor and the visible light imaging sensor being disposed to cause an amount of misalignment between a fluorescence image formation position and a visible light image formation position caused by the image-formation optical system to correspond to a difference between an optical path length of fluorescence and an optical path length of visible light, the fluorescence and the visible light forming the respective images via the color-separation-prism optical system, and,
where a focal length of the image-formation optical system is represented by f [mm], and an air-equivalent optical path length from the image-formation optical system to an imaging sensor is represented by Fb [mm], the image-formation optical system has the focal length and the air-equivalent optical path length that satisfy a condition represented by the following expression (1), $$Fb/f > 0.72 \quad \text{expression (1),}$$

the image-formation optical system includes, in order from object side to image side,
at least a diaphragm, a third lens group having a positive refractive power, and a second lens group having a positive refractive power,
the second lens group being a focus group configured to focus depending on an object distance,
the second lens group satisfies a relationship represented by the following expression (2), where a curvature radius at an object-side surface of a lens located on most object side in the third lens group is represented by R3 [mm], $$0.85 < R3/f \quad \text{expression (2).}$$

2. The scope optical system according to claim 1, wherein the image-formation optical system further includes, between the third lens group and the second lens group, a first lens group having a positive reflective power, and
the first lens group includes, in order from the object side to the image side, a lens having a negative refractive power with a concave surface facing the object side, and at least one lens having a positive refractive power,
the second lens group being a focus group configured to focus depending on an object distance, and
the image-formation optical system satisfies a condition represented by the following expression (3), where an air-equivalent optical path length from the image-formation optical system to the color-separation-prism optical system is represented by L [mm], $$1.4 < L/f < 1.8 \quad \text{expression (3).}$$

3. The scope optical system according to claim 2, wherein the image-formation optical system further includes, between the diaphragm and the first lens group, in order from the object side to the image side, a fourth lens group having a negative refractive power, and
the fourth lens group satisfies a condition represented by the following expression (4), where a focal length of the fourth lens group in the image-formation optical system is represented by f4 [mm], $$-0.80 < f4/f < -0.35 \quad \text{expression(4).}$$

4. The scope optical system according to claim 3, wherein the image-formation optical system further includes a fifth lens group having a negative refractive power at a subsequent stage of the second lens group.

5. The scope optical system according to claim 1, wherein the second lens group in the image-formation optical system further satisfies a condition represented by the following expression (5), where a focal length of the second lens group is represented by f2 [mm], $$1.0 < f2/f < 1.4 \quad \text{expression (5).}$$

6. The scope optical system according to claim 1, wherein the image-formation optical system satisfies a condition represented by the following expression (6), where a focal length at a fluorescence wavelength of the image-formation optical system is represented by f(NIR) [mm], and a focal length at a visible light wavelength of the image-formation optical system is represented by f(V) [mm], $$0.0025 < (f(NIR) - f(V))/f(V) < 0.0060 \quad \text{expression (6).}$$

7. The scope optical system according to claim 6, wherein the visible light imaging sensor is fixed at a position on an image-formation surface of the image-formation optical system, and
the fluorescence imaging sensor is fixed at a position in which an optical path difference satisfies the expression (6).

8. The scope optical system according to claim 6, wherein
the visible light imaging sensor is fixed at a position on an image-formation surface of the image-formation optical system,
the fluorescence imaging sensor is provided to allow a separation distance from the color-separation-prism optical system to be variable, and
the scope optical system further includes a fluorescence image focusing mechanism that varies an optical path difference to cause the expression (6) to be satisfied.

9. The scope optical system according to claim 1, wherein the color-separation-prism optical system includes
a color-separating prism including the dichroic film, and
a bandpass filter provided between the color-separating prism and the fluorescence imaging sensor, the bandpass filter having an entrance surface perpendicular to an optical axis.

10. The scope optical system according to claim 9, wherein
the dichroic film has a transmittance of 90% or more in a wavelength band of 780 to 880 nm, and a transmittance of 10% or less in a wavelength band of 400 to 720 nm, and
the bandpass filter has a transmittance of 90% or more in a wavelength band of 813 to 850 nm, and a transmittance of 10% or less in a wavelength band of 350 to 805 nm.

11. An imaging apparatus comprising a scope optical system, the scope optical system including
an image-formation optical system configured to form an image in each of wavelength bands to be formed in a predetermined imaging sensor, the wavelength bands including a fluorescence wavelength band belonging to a near-infrared light wavelength band and a visible light wavelength band,
a color-separation-prism optical system having a dichroic film constructed to separate an optical path of light to be imaged by the image-formation optical system into an optical path of the visible light wavelength band and an optical path of the fluorescence wavelength band,
a visible light imaging sensor configured to form an image of the visible light wavelength band, and
a fluorescence imaging sensor configured to form an image in the fluorescence wavelength band, wherein
the visible light imaging sensor and the fluorescence imaging sensor are disposed to cause an optical path difference between an optical path length of an optical path for visible light and an optical path length of an optical path for fluorescence to correspond to an amount of misalignment between a fluorescence image formation position and a visible light image formation position caused by the image-formation optical system, the visible light forming an image in the visible light imaging sensor via the color-separation-prism optical system, the fluorescence forming an image in the fluorescence imaging sensor via the color-separation-prism optical system, and,
where a focal length of the image-formation optical system is represented by f [mm], and an air-equivalent optical path length from the image-formation optical system to an imaging sensor is represented by Fb [mm], the image-formation optical system has the focal length and the air-equivalent optical path length that satisfy a condition represented by the following expression (1), $$Fb/f > 0.72 \quad \text{expression (1),}$$

the image-formation optical system includes, in order from object side to image side,
at least a diaphragm, a third lens group having a positive refractive power, and a second lens group having a positive refractive power,
the second lens group being a focus group configured to focus depending on an object distance, and
the second lens group satisfies a relationship represented by the following expression (2), where a curvature radius at an object-side surface of a lens located on most object side in the third lens group is represented by R3 [mm], $$0.85 < R3/f \quad \text{expression (2).}$$

12. The imaging apparatus according to claim 11, wherein
the image-formation optical system further includes, between the third lens group and the second lens group, a first lens group having a positive reflective power, and
the first lens group includes, in order from the object side to the image side, a lens having a negative refractive power with a concave surface facing the object side, and at least one lens having a positive refractive power,
the second lens group being a focus group configured to focus depending on an object distance, and
the image-formation optical system satisfies a condition represented by the following expression (3), where an air-equivalent optical path length from the image-formation optical system to the color-separation-prism optical system is represented by L [mm], $$1.4 < L/f < 1.8 \quad \text{expression (3).}$$

13. The imaging apparatus according to claim 12, wherein
the image-formation optical system further includes, between the diaphragm and the first lens group, in order from the object side to the image side, a fourth lens group having a negative refractive power, and
the fourth lens group satisfies a condition represented by the following expression (4), where a focal length of the fourth lens group in the image-formation optical system is represented by f4 [mm], $$-0.80 < f4/f < -0.35 \quad \text{expression (4).}$$

14. The imaging apparatus according to claim 13, wherein the image-formation optical system further includes a fifth lens group having a negative refractive power at a subsequent stage of the second lens group.

15. The imaging apparatus according to claim 11, wherein the image-formation optical system satisfies a condition represented by the following expression (5), where a focal length at a fluorescence wavelength of the image-formation optical system is represented by f(NIR) [mm], and a focal length at a visible light wavelength of the image-formation optical system is represented by f(V) [mm], $$0.0025 < (f(NIR) - f(V))/f(V) < 0.0060 \quad \text{expression (5).}$$

16. An endoscope unit comprising:
a scope configured to generate an image of a predetermined imaging target of a fluorescence wavelength band belonging to a near-infrared light wavelength band and an image of the predetermined imaging target of a visible light wavelength band;
an imaging system that includes a scope optical system coupled to the scope, a visible light imaging sensor in which the image of the visible light wavelength band is formed, and a fluorescence imaging sensor in which the image of the fluorescence wavelength band is formed, the imaging system being configured to generate a captured picture image of the imaging target of the fluorescence wavelength band and a captured picture image of the imaging target of the visible light wavelength band, wherein the scope optical system includes an image-formation optical system configured to form an image in each of the fluorescence wavelength band and the visible light wavelength band in a predetermined imaging sensor, and a color-separation-prism optical system having a dichroic film constructed to separate an optical path of light to be imaged by the image-formation optical system into an optical path of the visible light wavelength band and an optical path of the fluorescence wavelength band, the visible light imaging sensor and the fluorescence imaging sensor are disposed to cause an optical path difference between an optical path length of an optical path for visible light and an optical path length of an optical path for fluorescence to correspond to an amount of misalignment between a fluorescence image formation position and a visible light image formation position caused by the image-formation optical system, the visible light forming an image in the visible light imaging sensor via the color-separation-prism optical system, the fluorescence forming an image in the fluorescence imaging sensor via the color-separation-prism optical system, and, where a focal length of the image-formation optical system is represented by f [mm], and an air-equivalent optical path length from the image-formation optical system to an imaging sensor is represented by Fb [mm], the image-formation optical system has the focal length and the air-equivalent optical path length that satisfy a condition represented by the following expression (1), $Fb/f > 0.72$      expression (1), the image-formation optical system includes, in order from object side to image side, at least a diaphragm, a third lens group having a positive refractive power, and a second lens group having a positive refractive power, the second lens group being a focus group configured to focus depending on an object distance, and the second lens group satisfies a relationship represented by the following expression (2), where a curvature radius at an object-side surface of a lens located on most object side in the third lens group is represented by R3 [mm], $0.85 < R3/f$      expression (2).

17. The endoscope unit according to claim 16, wherein the image-formation optical system further includes, between the third lens group and the second lens group, a first lens group having a positive reflective power, and the first lens group includes, in order from the object side to the image side, a lens having a negative refractive power with a concave surface facing the object side, and at least one lens having a positive refractive power, the second lens group being a focus group configured to focus depending on an object distance, and the image-formation optical system satisfies a condition represented by the following expression (3), where an air-equivalent optical path length from the image-formation optical system to the color-separation-prism optical system is represented by L [mm], $1.4 < L/f < 1.8$      expression (3).

18. The endoscope unit according to claim 17, wherein the image-formation optical system further includes, between the diaphragm and the first lens group, in order from the object side to the image side, a fourth lens group having a negative refractive power, and the fourth lens group satisfies a condition represented by the following expression (4), where a focal length of the fourth lens group in the image-formation optical system is represented by f4 [mm], $-0.80 < f4/f < -0.35$      expression (4).

19. The endoscope unit according to claim 18, wherein the image-formation optical system further includes a fifth lens group having a negative refractive power at a subsequent stage of the second lens group.

20. The endoscope unit according to claim 16, wherein the second lens group in the image-formation optical system further satisfies a condition represented by the following expression (5), where a focal length of the second lens group is represented by f2 [mm], $1.0 < f2/f < 1.4$      expression (5).

21. The endoscope unit according to claim 16, wherein the image-formation optical system satisfies a condition represented by the following expression (6), where a focal length at a fluorescence wavelength of the image-formation optical system is represented by f(NIR) [mm], and a focal length at a visible light wavelength of the image-formation optical system is represented by f(V) [mm], $0.0025 < (f(NIR) - f(V))/f(V) < 0.0060$      expression (6).

* * * * *